US011396534B2

(12) United States Patent
Choi et al.

(10) Patent No.: US 11,396,534 B2
(45) Date of Patent: Jul. 26, 2022

(54) INSULIN ANALOGS WITH REDUCED AFFINITY TO INSULIN RECEPTOR AND USE THEREOF

(71) Applicants: HANMI PHARM. CO., LTD., Hwaseong-si (KR); Sanofi-Aventis Deutschland GmbH, Frankfurt am Main (DE)

(72) Inventors: In Young Choi, Hwaseong-si (KR); Sung Youb Jung, Hwaseong-si (KR); Marcus Korn, Frankfurt am Main (DE); Stefan Guessregen, Frankfurt am Main (DE); Norbert Tennagels, Frankfurt am Main (DE)

(73) Assignees: HANMI PHARM. CO., LTD., Hwaseong-si (KR); SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days.

(21) Appl. No.: 16/335,490

(22) PCT Filed: Sep. 22, 2017

(86) PCT No.: PCT/KR2017/010504
§ 371 (c)(1),
(2) Date: Mar. 21, 2019

(87) PCT Pub. No.: WO2018/056764
PCT Pub. Date: Mar. 29, 2018

(65) Prior Publication Data
US 2019/0300593 A1 Oct. 3, 2019

(30) Foreign Application Priority Data
Sep. 23, 2016 (KR) .................. 10-2016-0122484

(51) Int. Cl.
| | |
|---|---|
| *C07K 14/62* | (2006.01) |
| *A61K 38/28* | (2006.01) |
| *C07K 1/20* | (2006.01) |
| *C07K 1/12* | (2006.01) |
| *C07K 1/18* | (2006.01) |
| *C12P 21/00* | (2006.01) |
| *C12N 15/70* | (2006.01) |
| *A61K 38/00* | (2006.01) |

(52) U.S. Cl.
CPC ............. *C07K 14/62* (2013.01); *A61K 38/28* (2013.01); *C07K 1/12* (2013.01); *C07K 1/18* (2013.01); *C07K 1/20* (2013.01); *C12N 15/70* (2013.01); *C12P 21/00* (2013.01); *A61K 38/00* (2013.01)

(58) Field of Classification Search
CPC ........................ C07K 14/62; A61K 38/28
See application file for complete search history.

(56) References Cited

U.S. PATENT DOCUMENTS

| | | |
|---|---|---|
| 5,175,145 A | 12/1992 | Cooper |
| 5,422,339 A | 6/1995 | Eisenbarth et al. |
| 5,424,286 A | 6/1995 | Eng |
| 5,716,927 A | 2/1998 | Balschmidt et al. |
| 6,403,764 B1 | 6/2002 | Dubaquie et al. |
| 7,736,653 B2 | 6/2010 | Kim et al. |
| 7,790,677 B2 | 9/2010 | Zimmerman et al. |
| 8,476,230 B2 | 7/2013 | Song et al. |
| 8,691,759 B2* | 4/2014 | Madsen .............. A61P 5/48 514/5.9 |
| 8,703,701 B2 | 4/2014 | DiMarchi |
| 9,018,161 B2* | 4/2015 | Nielsen ............... A61P 3/06 514/5.9 |
| 9,165,768 B2 | 10/2015 | Kang |
| 9,260,502 B2* | 2/2016 | Nielsen ............... A61P 3/10 |
| 9,341,445 B2 | 5/2016 | de Haas et al. |
| 9,422,349 B2 | 8/2016 | Jung et al. |
| 9,526,764 B2 | 12/2016 | Werner et al. |
| 9,528,180 B2 | 12/2016 | Becker et al. |
| 9,669,073 B2 | 6/2017 | Kim et al. |
| 2005/0288248 A1 | 12/2005 | Pan et al. |
| 2006/0241019 A1 | 10/2006 | Bridon et al. |
| 2009/0306337 A1 | 12/2009 | Madsen et al. |
| 2010/0105877 A1 | 4/2010 | Song et al. |
| 2010/0216692 A1 | 8/2010 | Brunner-Schwarz et al. |
| 2011/0077197 A1 | 3/2011 | Habermann et al. |
| 2011/0152185 A1 | 6/2011 | Plum et al. |
| 2011/0257091 A1 | 10/2011 | DiMarchi et al. |
| 2012/0021978 A1 | 1/2012 | Werner et al. |
| 2012/0071402 A1 | 3/2012 | Madsen et al. |
| 2012/0100141 A1 | 4/2012 | Herring et al. |
| 2012/0184488 A1 | 7/2012 | Weiss |
| 2013/0028918 A1 | 1/2013 | Song et al. |
| 2013/0122023 A1 | 5/2013 | Woo et al. |
| 2014/0120120 A1 | 5/2014 | Woo et al. |

(Continued)

FOREIGN PATENT DOCUMENTS

| | | |
|---|---|---|
| CL | 1235-2003 | 4/2004 |
| CL | 0018-2009 | 6/2009 |

(Continued)

OTHER PUBLICATIONS

Chu et al., J. Prot. Chem. 11: 571-577, 1992.*
Wells, 1990, Biochemistry 29:8509-8517.*
Ngo et al., The Protein Folding Problem and Tertiary Structure Prediction, 1994, pp. 492-495.*
Senshang Lin, et al., "Comparative Pharmacokinetic and Pharmacodynamic Studies of Human Insulin and Analogues in Chronic Diabetic Yucatan Minipigs", The Journal of Pharmacology and Experimental Therapeutics, 1998, pp. 959-966, vol. 286, No. 2.

(Continued)

*Primary Examiner* — Gyan Chandra
(74) *Attorney, Agent, or Firm* — Sughrue Mion, PLLC

(57) ABSTRACT

The present invention relates to a novel insulin analog, use thereof, and a method for preparing the analog.

11 Claims, 7 Drawing Sheets

Specification includes a Sequence Listing.

(56) References Cited

U.S. PATENT DOCUMENTS

| | | | |
|---|---|---|---|
| 2014/0212440 A1 | 7/2014 | Jung et al. | |
| 2015/0190528 A1 | 7/2015 | Lim et al. | |
| 2016/0000931 A1 | 1/2016 | Jang et al. | |
| 2016/0008483 A1 | 1/2016 | Hwang et al. | |
| 2017/0066811 A1 | 3/2017 | Kim et al. | |
| 2017/0101455 A1 | 4/2017 | Jung et al. | |
| 2017/0143802 A1* | 5/2017 | Kim | A61K 38/28 |
| 2017/0196943 A1 | 7/2017 | Jung et al. | |
| 2018/0282388 A1 | 10/2018 | Kim et al. | |
| 2018/0291077 A1* | 10/2018 | Choi | B01D 15/362 |
| 2020/0101171 A1 | 4/2020 | Park et al. | |

FOREIGN PATENT DOCUMENTS

| | | |
|---|---|---|
| CL | 201603075 | 11/2016 |
| CN | 1571676 A | 1/2005 |
| CN | 1635900 A | 7/2005 |
| CN | 101743252 A | 6/2010 |
| CN | 101861333 A | 10/2010 |
| CN | 102256618 A | 11/2011 |
| CN | 102711805 A | 10/2012 |
| CN | 103596584 A | 2/2014 |
| CN | 103596595 A | 2/2014 |
| CN | 103732616 A | 4/2014 |
| CN | 103736082 A | 4/2014 |
| DE | 25 36 040 A1 | 2/1977 |
| DE | 10227232 A1 | 1/2004 |
| DE | 102008003568 A1 | 7/2009 |
| DE | 102008025008 A1 | 11/2009 |
| EA | 201690116 A1 | 7/2016 |
| EP | 2017288 A1 | 1/2009 |
| EP | 2279758 A2 | 2/2011 |
| EP | 2700654 A1 | 2/2014 |
| EP | 2963056 A1 | 1/2016 |
| EP | 3 028 399 A1 | 6/2016 |
| JP | 4-502465 A | 5/1992 |
| JP | 2009-504169 A | 2/2009 |
| JP | 2010-504087 A | 2/2010 |
| JP | 2010-533671 A | 10/2010 |
| JP | 2011-512856 A | 4/2011 |
| JP | 2011-515358 A | 5/2011 |
| JP | 2012-62311 A | 3/2012 |
| JP | 2012-229214 A | 11/2012 |
| JP | 2013-533864 A | 8/2013 |
| JP | 2015-509950 A | 4/2015 |
| KR | 10-2005-0121748 A | 12/2005 |
| KR | 10-0725315 B1 | 6/2007 |
| KR | 10-2010-0111683 A | 10/2010 |
| KR | 10-2011-0084956 A | 7/2011 |
| KR | 10-2011-0092253 A | 8/2011 |
| KR | 10-1058209 B1 | 8/2011 |
| KR | 10-1058290 B1 | 8/2011 |
| KR | 10-2011-0111267 A | 10/2011 |
| KR | 10-2011-0134210 A | 12/2011 |
| KR | 10-2011-0137819 A | 12/2011 |
| KR | 1020110134209 A | 12/2011 |
| KR | 10-2012-0135123 A | 12/2012 |
| KR | 10-2012-0137271 A | 12/2012 |
| KR | 10-2012-0139579 A | 12/2012 |
| KR | 10-1231431 B1 | 2/2013 |
| KR | 10-1324828 B1 | 11/2013 |
| KR | 10-1330868 B1 | 11/2013 |
| KR | 10-2014-0006938 A | 1/2014 |
| KR | 10-2014-0022909 A | 2/2014 |
| KR | 10-2014-0106452 A | 9/2014 |
| KR | 10-2015-0087130 A | 7/2015 |
| KR | 10-2015-0138101 A | 12/2015 |
| KR | 10-2016-0001391 A | 1/2016 |
| KR | 10-2016-0007295 A | 1/2016 |
| TW | 201204382 A1 | 2/2012 |
| TW | 201410704 A | 3/2014 |
| TW | 201520224 A | 6/2015 |
| WO | 96/32478 A1 | 10/1996 |
| WO | 97/34631 A1 | 9/1997 |
| WO | 2008034881 A1 | 3/2008 |
| WO | 2008/145721 A2 | 12/2008 |
| WO | 2009/022005 A1 | 2/2009 |
| WO | 2009/063072 A2 | 5/2009 |
| WO | 2009112583 A2 | 9/2009 |
| WO | 2009/129250 A2 | 10/2009 |
| WO | 2010/043566 A3 | 4/2010 |
| WO | 2010/080606 A1 | 7/2010 |
| WO | 2010/080609 A1 | 7/2010 |
| WO | 2011/028813 A2 | 3/2011 |
| WO | 2011/075606 A2 | 6/2011 |
| WO | 2011122921 A2 | 10/2011 |
| WO | 2012/015692 A2 | 2/2012 |
| WO | 2012/098462 A1 | 7/2012 |
| WO | 2012/165915 A2 | 12/2012 |
| WO | 2012/167251 A1 | 12/2012 |
| WO | 2012/169798 A2 | 12/2012 |
| WO | 2012/173422 A1 | 12/2012 |
| WO | 2013/110069 A1 | 7/2013 |
| WO | 2013/133667 A1 | 9/2013 |
| WO | 2014/017843 A1 | 1/2014 |
| WO | 2014/017845 A2 | 1/2014 |
| WO | 2014/017847 A1 | 1/2014 |
| WO | 2014/017849 A1 | 1/2014 |
| WO | 2014/049610 A2 | 4/2014 |
| WO | 2014/073842 A1 | 5/2014 |
| WO | 2014073845 A1 | 5/2014 |
| WO | 2014/133324 A1 | 9/2014 |
| WO | 2015/013745 A1 | 2/2015 |
| WO | 2015108398 A1 | 7/2015 |
| WO | 2015/183038 A1 | 12/2015 |
| WO | 2015199511 A1 | 12/2015 |
| WO | 2016/006963 A1 | 1/2016 |
| WO | 2017/052305 A1 | 3/2017 |

OTHER PUBLICATIONS

Jens Brange, MSC, et al., "Monomeric Insulins and Their Experimental and Clinical Implications", Diabetes Care, Sep. 1990, pp. 923-954, vol. 13, No. 9.

Ulla Ribel, et al., "Equivalent In Vivo Biological Activity of Insulin Analogues and Human Insulin Despite Different In Vitro Potencies", Diabetes, Sep. 1990, pp. 1033-1039, vol. 39.

International Search Report for PCT/KR2017/010504 dated Jan. 31, 2018 (PCT/ISA/210).

United States Patent and Trademark Office Restriction Requirement dated May 30, 2019 in U.S. Appl. No. 15/983,923.

R. Vigneri, et al., "Insulin and its analogs: actions via insulin and IGF receptors", Acta Diabetol, 2010, pp. 271-278, vol. 47, No. 4.

NCBI, "insulin preproprotein [*Homo sapiens*]", NCBI Reference Sequence: NP_000198.1, Feb. 17, 2013, [online]<http://www.ncbi.nlm.nih.gov/protein/4557671?sat=17&satkey=22757282> retrieved on Mar. 31, 2014, 2 pages.

United States Patent and Trademark Office Restriction Requirement dated Jan. 10, 2018 in U.S. Appl. No. 15/315,020.

United States Patent and Trademark Office Notice of Allowance dated Sep. 7, 2018 in U.S. Appl. No. 15/315,020.

International Searching Authority, International Search Report of PCT/KR2018/003489 dated Oct. 29, 2018.

International Searching Authority, International Search Report for PCT/KR2014/001593 dated May 22, 2014.

International Searching Authority, Written Opinion of the International Search Authority for PCT/KR2014/001593 dated May 22, 2014.

Chile Patent Office, Communication dated Aug. 22, 2016, issued in Chilean Application No. 2015-002330.

European Patent Office; Communication dated Nov. 30, 2016, in European Application No. 14757629.2.

Colombian Patent Office; Communication dated Novembers, 2016, in Columbian application No. 15227010.

European Patent Office; Communication dated May 10, 2017, in European application No. 14757629.2.

Chilean Patent Office, Communication dated Jul. 13, 2017 by the Chilean Patent Office in Chilean Patent Application No. 201601844.

European Patent Office, Communication dated Sep. 20, 2017 by the European Patent Office in Application No. EP 15 73 7856.3.

(56) References Cited

OTHER PUBLICATIONS

Authier F. et al. (1998) "Uptake and Metabolic Fate of [His$^{48}$, His$^{B4}$, Glu$^{B10}$, His$^{B27}$] Insulin in Rat Liver In Vivo," Biochem J. 332;421-30.
Duckworth, W.C. et al. (Oct. 1998). "Insulin Degradation: Process and Potential," Endocr Rev. 19(5):608-24.
Valera, M. M. et al. (Dec. 2003). "Insulin Clearance in Obesity," J Am Coll Nutr. 22(6):487-93, Abstract Only.
United States Patent and Trademark Office communication dated Sep. 14, 2017 in U.S. Appl. No. 15/250,459.
UniProtKB A6XGL2, pp. 1-5. Integrated in UniProtKB/TrEMBL Aug. 21, 2007.
Keller, D. et al. (2001). "Flexibility and Bioactivity of Insulin: an NMR Investigation of the Solution Structure and Folding of an Unusually Flexible Human Insulin Mutant with Increased Biological Activity," Biochemistry 40(35):10732-10740.
NCBI, Genbank AAA72172.1, (Apr. 27, 1993)/ "Synthetic Preproinsulin [synthetic construct] NCBI," located at https://www.ncbi.nlm.nih.gov/protein/AAA72172.1?report=gpwithparts&log$=se qview, last visited on Jun. 20, 2017, 1 pages.
NCBI, Genbank AKI70564.1 (Jun. 1, 2015). "INS, Partial [synthetic construct]" located at <https://www.ncbi.nlm.nih.gov/protein/AKI70564.1?report= gpwithparts&log$=seqview> last visited on Jun. 20, 2017, 2 pages.
NCBI, Genbank NM_001291897.1, (May 13, 2015). "*Homo sapiens* Insulin (INS), Transcript Variant 4, mRNA," located at < https://www.ncbi.nlm.nih.gov/nuccore/NM-001291897.1?report= gpwithparts&log$=seqview&sat=4&satkey=139944924>, last visited on Jun. 20, 2017, 3 pages.
Yampolsky et al., "The Exchangeability of Amino Acids in Proteins," Genetics, 170: 1459-1472, 2005.
Rudinger J., "Characteristics of the Amino Acids as Components of a Peptide Hormone Sequence," Peptide Hormones, J.A. Parsons Edition, University Park Press, Jun. 1976, pp. 1-7. (8 pages total).
"Designing Custom Peptides," from Sigma Genosys, pp. 1-2. Accessed Dec. 16, 2004.
Schinzel R., Drueckes P., "The Phosphate Recognition Site of *Escherichia coli* Maltodextrin Phosphorylase," FEBS, Jul. 1991. 286(1,2): 125-128.
Berendsen HJC, "A Glimpse of the Holy Grail?" Science, 1998, 282: 642-643.
Voet D, Voet JG, Biochemistry, Second Edition, John Wiley & Sons, Inc., 1995, pp. 235-241. (9 pages).
Ngo J.T., Marks J, Karplus M., "Computational Complexity, Protein Structure Prediction, and the Levinthal Paradox," The Protein Folding Problem and Tertiary Structure Prediction, K. Merc Jr. and S. Le Grand Editiors, 1994, pp. 491-495.
Bradley CM, Barrick D, "Limits of Cooperativity in a Structurally Modular Protein Response of the Notch Ankyrin Domain to Analogous Alanine Substitutions in Each Repeat," J. Mol. Biol., 2002, 324: 373-386.
Betts et al., "Amino Acid Properties and Consequences of Substitutions," Bioinformatics for Geneticists, Chapter 14, John Wiley & Sons, Ltd., 2003, pp. 289-316.
Jørgensen, A. et al. (Apr. 1996). "Solution Structure of the Superactive Monomeric Des-[Phe(B25)] Human Insulin Mutant: Elucidation of the Structural Basis for the Monomerization of Des-[Phe(B25)] Insulin and the Dimerization of Native Insulin," J. Mol. Biol.,257(3):684-699.
Uhlmann, E. et al. (Jun. 1990). "Antisense Oligonucleotides: A New Therapeutic Principle," Chemical Reviews 90(4):543-584.
United States Patent and Trademark Office Non-Final Office Action dated Sep. 8, 2017 in U.S. Appl. No. 15/313,501.
Martin Lorenz et al., "Recent progress and future options in the development of GLP-1 receptor agonists for the treatment of diabesity", Bioorganic & Medicinal Chemistry Letters, 2013, pp. 4011-4018, vol. 23, No. 14.
International Searching Authority, International Search Report of PCT/KR2015/005455 dated Aug. 24, 2015 [PCT/ISA/210].

International Searching Authority, Written Opinion of PCT/KR2015/005455 dated Aug. 24, 2015 [PCT/ISA/237].
Colombian Patent Office; Communication dated Aug. 24, 2017, in Colombian application No. 15227010.
Taiwanese Intellectual Property Office; Communication dated Sep. 11, 2017 in application No. 103106674.
Intellectual Property Office of Singapore, Communication dated Oct. 3, 2017 in application No. 11201609564T.
European Patent Office, Communication dated Nov. 10, 2017 in application No. 15799334.6.
Fosgerau et al., "Combination of Long-Acting Insulin with the Dual GluGLP-1 Agonist ZP2929 Causes Improved Glycemic Control without Body Weight Gain in db/db Mice", 1527-P, Diabetes (Suppl 1), vol. 60, 2011, p. A418, XP-002775063.
European Patent Office; Communication dated Nov. 17, 2017 in application No. 15799077.1.
United States Patent and Trademark Office; Notice of Allowance dated Feb. 26, 2018 in U.S. Appl. No. 15/250,459.
United States Patent and Trademark Office; Non-Final Office Action dated Jan. 16, 2018 in U.S. Appl. No. 15/113,027.
United States Patent and Trademark Office; Final Rejection dated Mar. 8, 2018 in U.S. Appl. No. 15/313,501.
Japanese Patent Office; Communication dated Jan. 16, 2018 in Japanese application No. 2015-559199.
Saudi Arabian Patent Office, Communication dated Apr. 30, 2016 issued in Application No. 515360933.
Intellectual Property Office of Singapore; Communication dated Jan. 29, 2018 in application No. 11201609872Y.
United States Patent and Trademark Office; Non-Final Office Action dated Apr. 17, 2018 in U.S. Appl. No. 15/315,020.
Colombian Patent and Trademark Office; communication dated Feb. 16, 2018, in Colombian application No. NC2016/0004794.
Kristensen et al., "Alanine Scanning Mutagenesis of Insulin," J. Biol. Chem. 272:12978-12983 (1997).
Chen et al., "Four new monomeric insulins obtained by alanine scanning the dimer-forming surface of the insulin molecule," Protein Eng'g 13:779-782 (2000).
Nakagawa et al., "Chiral Mutagenesis of Insulin, Contribution of the B20-B23 β-turn to activity and stability," J. Biol. Chem. 281: 22386-22396, (2006).
Chu et al., "The A14 Position of Insulin Tolerates Considerable Structural Alterations with Modest Effects on the Biological Behavior of the Hormone," J. Prot. Chem. 11:571-577 (1992).
Mohan, "Which insulin to use? Human or animal?," Curr. Sci. 83:1544-1547 (2002).
Chinese Patent and Trademark Office; communication dated Mar. 1, 2018, in Chinese Patent Application No. 201480006998.4.
Chilean Patent Office; Communication dated May 29, 2018 issued in Chilean Application No. 201603069.
Ukraine Patent Office; Communication dated Jul. 2, 2018 in application No. 12469/3A/18.
Intellectual Property Office of Taiwan; Communication dated Jun. 29, 2018 in application No. 106143717.
Intellectual Property Office of the Dominican Republic; Communication dated Jul. 26, 2018 in application No. P2016-176.
Japanese Patent Office; Communication dated Sep. 11, 2018 in application No. 2015-559199.
Glendorf et al., "Engineering of Insulin Receptor Isoform-Selective Insulin Analogues", PLOS One, vol. 6, Issue 5, e20288, May 2011, 7 pages total.
Chilean Patent Office; Communication dated Nov. 14, 2018 issued in application No. 201603069.
Japanese Patent Office: Communication dated Nov. 13, 2018 in application No. 2016-564933.
Japanese Patent Office; Communication dated Mar. 5, 2019 in application No. 2016-569949.
Intellectual Property Office of Taiwan; Communication dated May 1, 2019 in application No. 104117389.
Intellectual Property Office of Singapore; Communication dated Apr. 5, 2019 in application No. 11201609872Y.

(56) References Cited

OTHER PUBLICATIONS

Wolfgang Glaesner et al., "Engineering and characterization of the long-acting glucagon-like peptide-1 analogue LY2189265, an Fc fusion protein", Diabetes/Metabolism Research and Reviews, vol. 26, 2010, pp. 287-296.
"CADTH Optimal Use Report: Combination Use of Insulin and Incretins in Type 2 Diabetes", Canadian Agency for Drugs and Technologies in Health, vol. 3, Issue 1C, Jul. 2013, pp. i-ii, 1-18 (22 pages total).
Fabio Selis et al., "Enzymatic mono-pegylation of glucagon-like peptide 1 towards long lasting treatment of type 2 diabetes", Results in Pharma Sciences 2, Elsevier, 2012, pp. 58-65.
C. Schmid et al., "Increased insulin dose requirement of long-acting insulin analogues in obese patients with type 2 diabetes", Diabetologia, vol. 52, 2009, pp. 2668-2669.
Bhat et al., "A novel GIP-oxyntomodulin hybrid peptide acting through GIP, glucagon and GLP-1 receptors exhibits weight reducing and anti-diabetic properties", Biochem Pharmacol, Jun. 1, 2013, vol. 85 No. 11, pp. 1655-1662.
Intellectual Property Office of Singapore; Communication dated Jul. 15, 2019 in application No. 11201802523X.
Ministry of Law and Human Rights Republic of Indonesia; Communication dated Jun. 12, 2019 in application No. P00201608768.
Intellectual Property Office of Taiwan; Communication dated May 13, 2019 in application No. 104117391.
European Patent Office; Communication dated Jul. 19, 2019 in application No. 16842233.5.
Pocai, "Unraveling oxyntomodulin, GLP1's enigmatic brother", Journal of Endocrinology, vol. 215, No. 3, pp. 335-346, Sep. 27, 2012.
Hinds et al., "Effects of PEG conjugation on insulin properties", Advanced Drug Delivery Reviews, vol. 54, No. 4, pp. 505-530, 2002.
Thibaudeau et al., "Synthesis and Evaluation of Insulin—Human Serum Albumin Conjugates", Bioconjugate Chemistry, American Chemical Society, vol. 16, No. 4, pp. 1000-1008, Jun. 25, 2005.
European Patent Office, Communication dated Sep. 20, 2017 by the European Patent Officer in application No. EP 15 73 7856.3.
United States Patent and Trademark Office communication dated Jul. 19, 2017 in U.S. Appl. No. 14/769,495.
United States Patent and Trademark Office communication dated Jan. 17, 2017 in U.S. Appl. No. 14/769,495.
United States Patent and Trademark Office communication dated Apr. 5, 2018 in U.S. Appl. No. 14/769,495.
United States Patent and Trademark Office communication dated Jul. 17, 2018 in U.S. Appl. No. 15/113,027.
Intellectual Property Office of Taiwan; Communication dated Jul. 2, 2018 in application No. 106143717.
Japanese Patent Office; Communication dated Jul. 4, 2019 in application No. 2016-570276.
United States Patent and Trademark Office Notice of Allowance dated Jan. 15, 2020 in U.S. Appl. No. 15/990,495.
United States Patent and Trademark Office Non-Final Office Action dated Aug. 23, 2019 in U.S. Appl. No. 15/990,495.
United States Patent and Trademark Office Restriction Requirement dated Apr. 22, 2019 in U.S. Appl. No. 15/990,495.
United States Patent and Trademark Office; Notice of Allowance dated Nov. 8, 2018 in U.S. Appl. No. 15/113,027.
United States Patent and Trademark Office; Final Office Action dated Jul. 17, 2018 in U.S. Appl. No. 15/113,027.
United States Patent and Trademark Office Restriction Requirement dated Jul. 18, 2017 in U.S. Appl. No. 15/113,027.
United States Patent and Trademark Office Notice of Allowance dated Aug. 7, 2018 in U.S. Appl. No. 15/313,501.
Extended European Search Report dated May 7, 2020 in European Application No. 17853478.0.
Epstein, "Non-randomness of Amino-acid Changes in the Evolution of Homologous Proteins", Nature Publishing Group, vol. 215, Jul. 22, 1967, pp. 355-359.
Glendorf et al., "Importance of the Solvent-Exposed Residues of the Insulin B Chain α-Helix for Receptor Binding", Biochemistry, 2008, vol. 47, No. 16, pp. 4743-4751 (9 pages total).
Affholter et al., "Identification of Residues in the Insulin Molecule Important for Binding to Insulin-Degrading Enzyme", Biochemistry, 1990, vol. 29, No. 33, pp. 7727-7733 (7 pages total).
Cockram CS et al., "The Biological Properties of Insulins with Tyrosine Replaced by Phenylalanine at Positions 14 and 19 of the A Chain" Diabet. Med., 1985, vol. 2, No. 4, p. 241-244 ( 4 pages total).
Miroslav Baudys et al., "Extending Insulin Action in Vivo by Conjugation to Carboxymethyl Dextran", Bioconjugate Chem., American Chemical Society, vol. 9, No. 2, Feb. 5, 1998, pp. 176-183 (8 pages total).
Fosgerau et al., "The new glucagon-GLP-1 dual agonist ZP2929 in combination with long-acting insulin improves glycemic control without causing weight gain in db/db mice", American Diabetes Association (ADA,) 71st Scientific Session, Jun. 24-28, 2011, 1 page.
Karounos, D. G. et al., "Metabolically inactive insulin analog prevents type 1 diabetes in prediabetic NOD mice", J. Clin. Invest., 1997, vol. 100, No. 6, pp. 1344-1348.
Gauguin, L. et al., "Structural Basis for the Lower Affinity of the Insulin-like Growth Factors for the Insulin Receptor", J. Biol. Chem., 2008, vol. 283, No. 5, pp. 2604-2613.
Kobayashi, "Diabetes: Diagnosis and Treatment Progress. III. Recent Topics Surrounding Diabetes. 1. Insulin gene and abnormality thereof", Nihon Pharmaceutical Society, Aug. 10, 1991, vol. 80, No. 8, pp. 75-79 (7 pages total).

* cited by examiner

[FIG. 1]
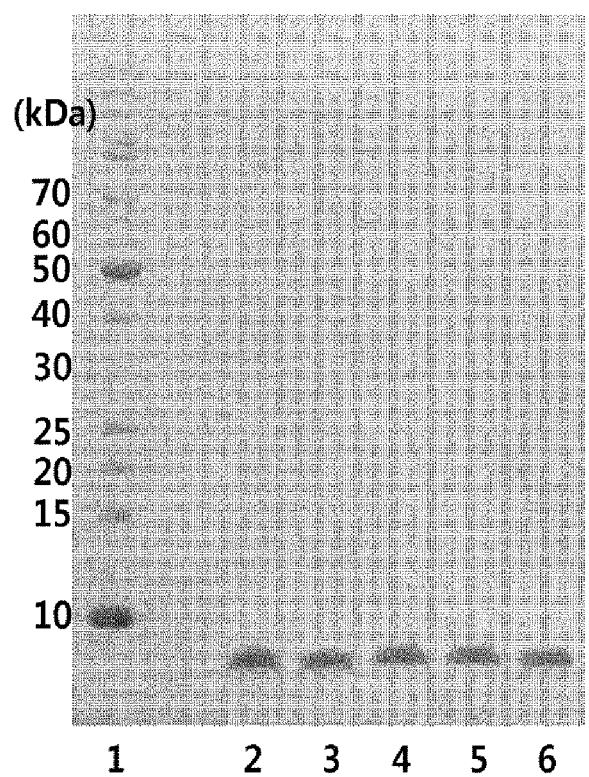

[FIG. 2a]
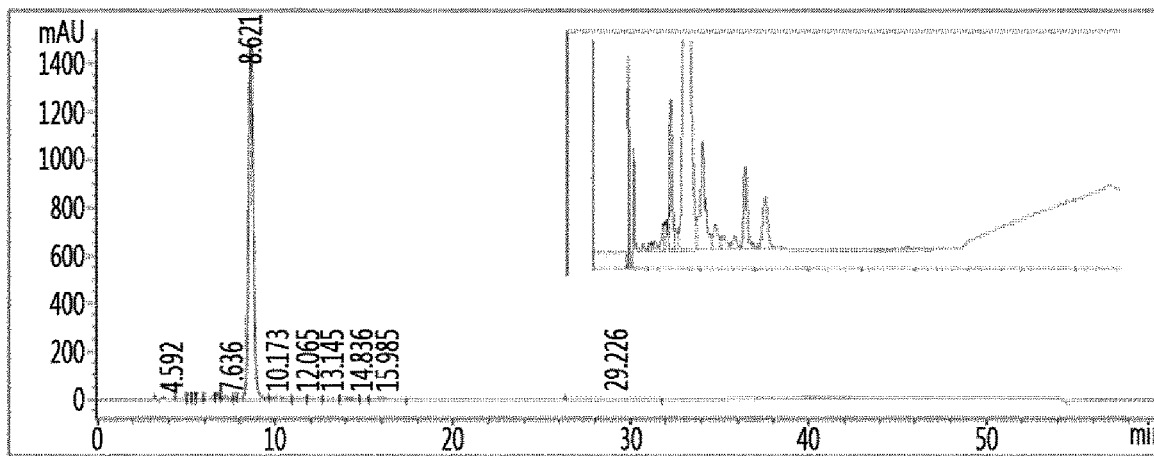
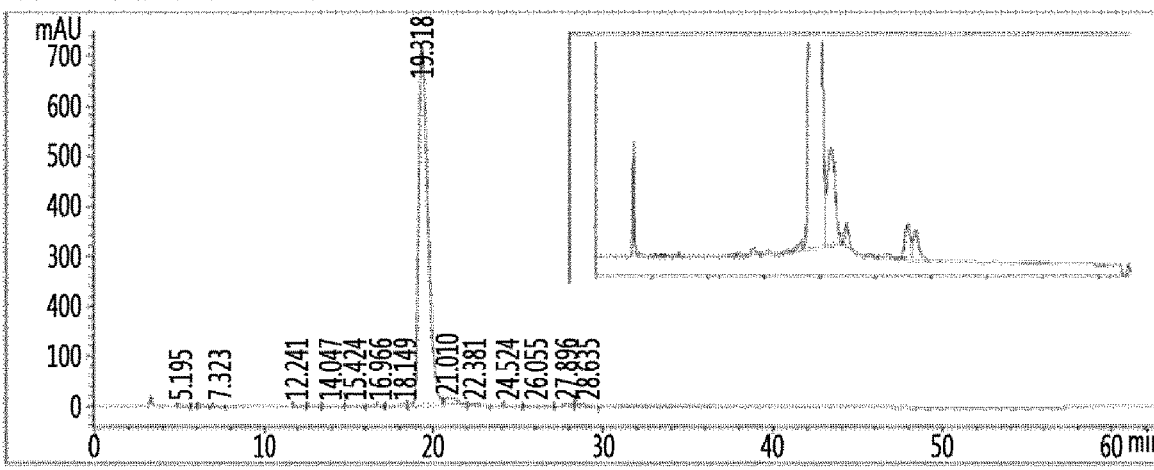
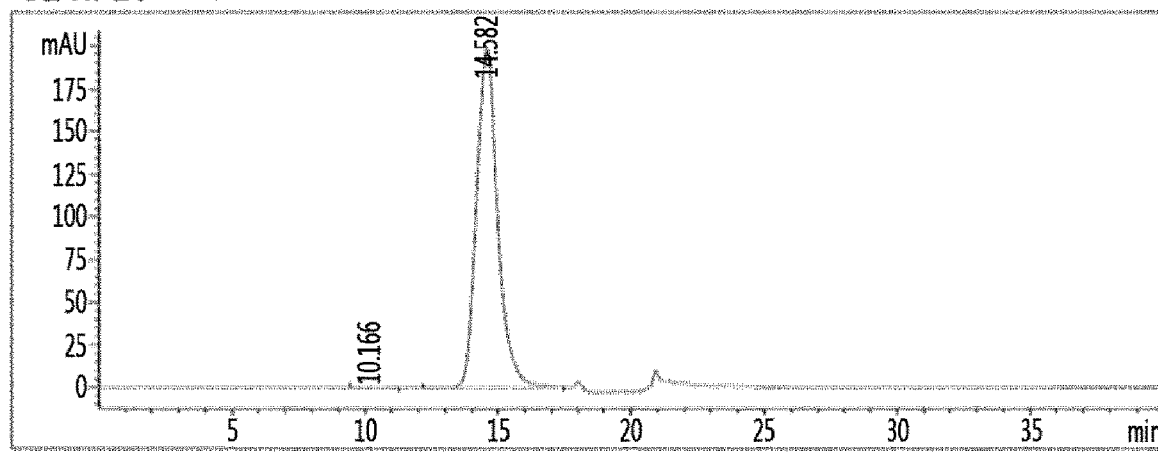

[FIG. 2b]
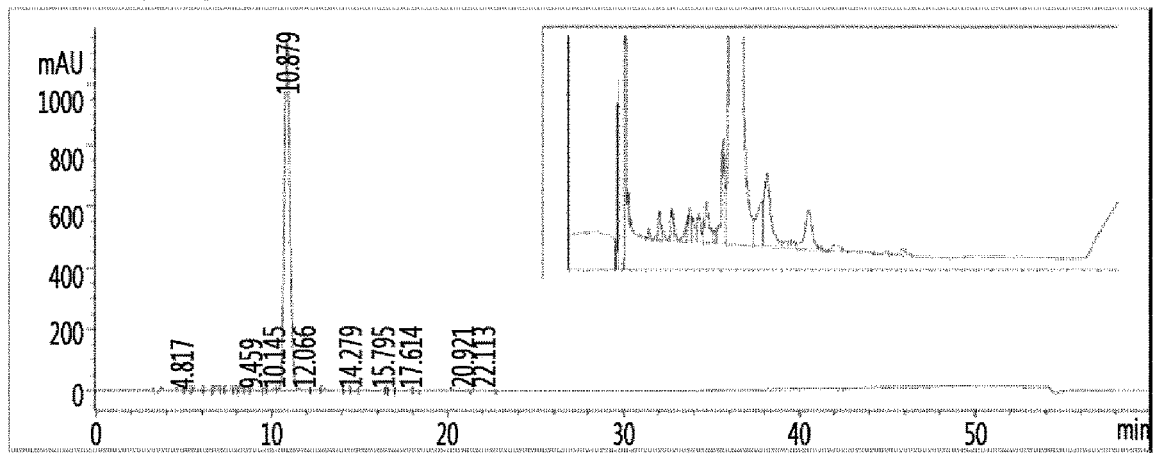
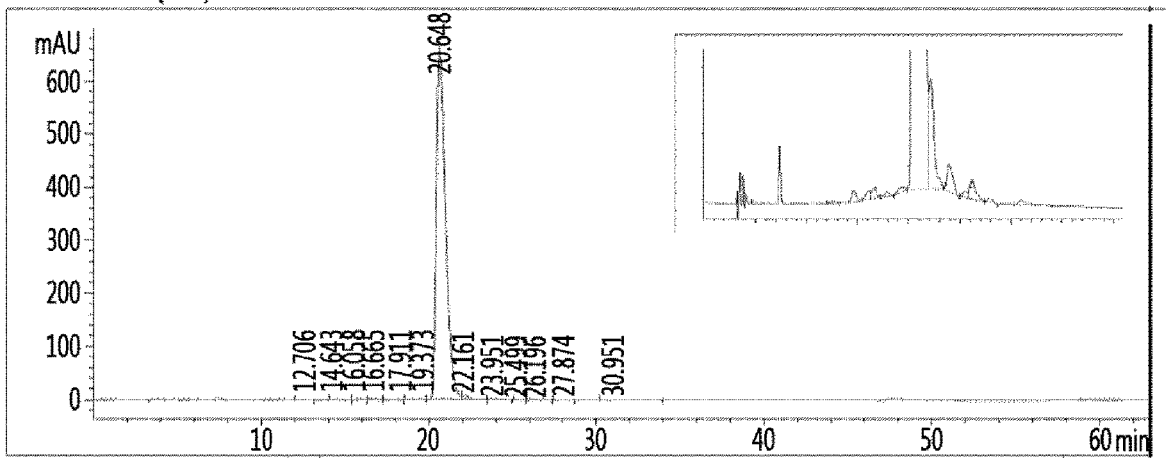
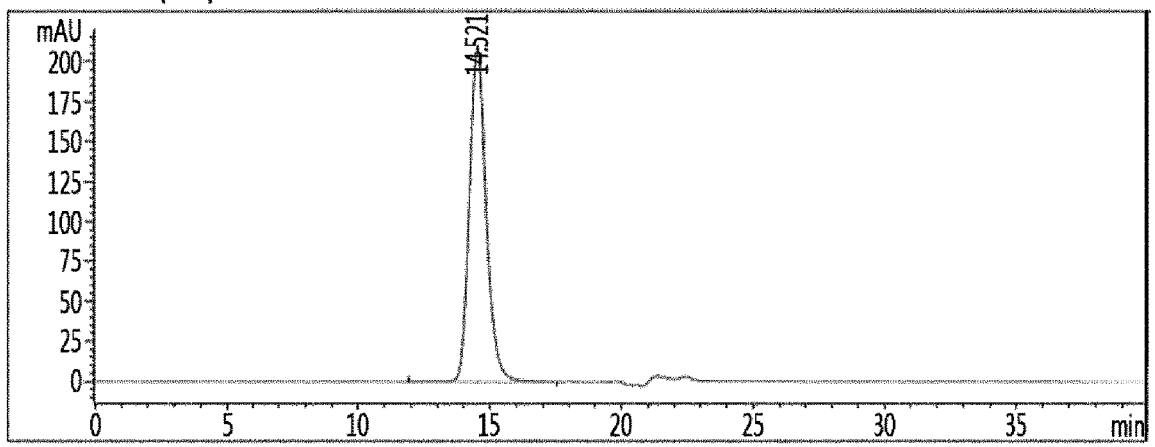

[FIG. 2c]
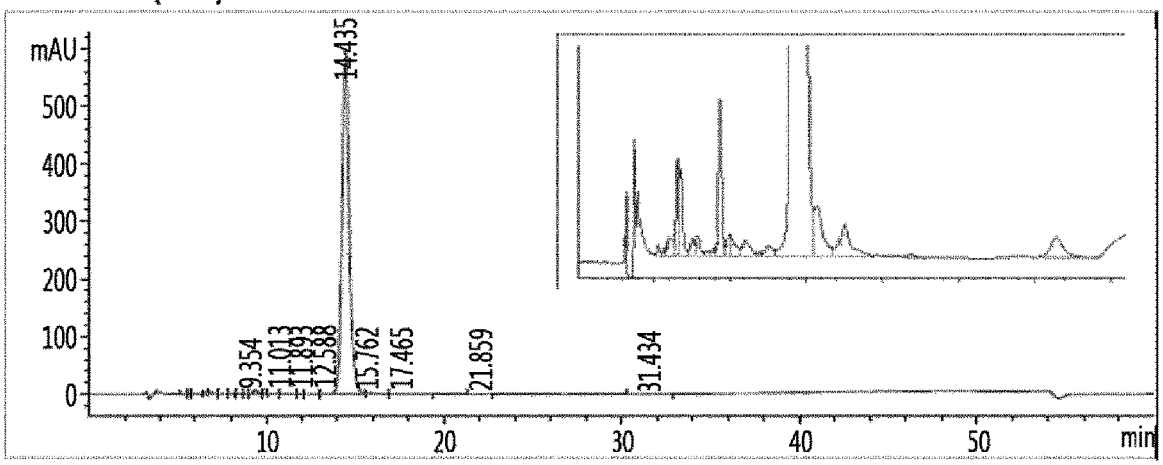
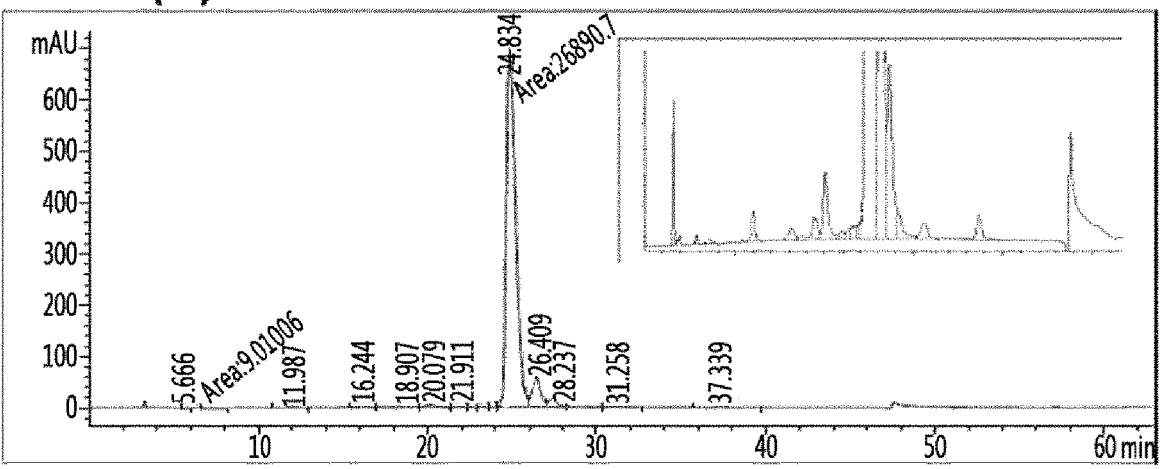
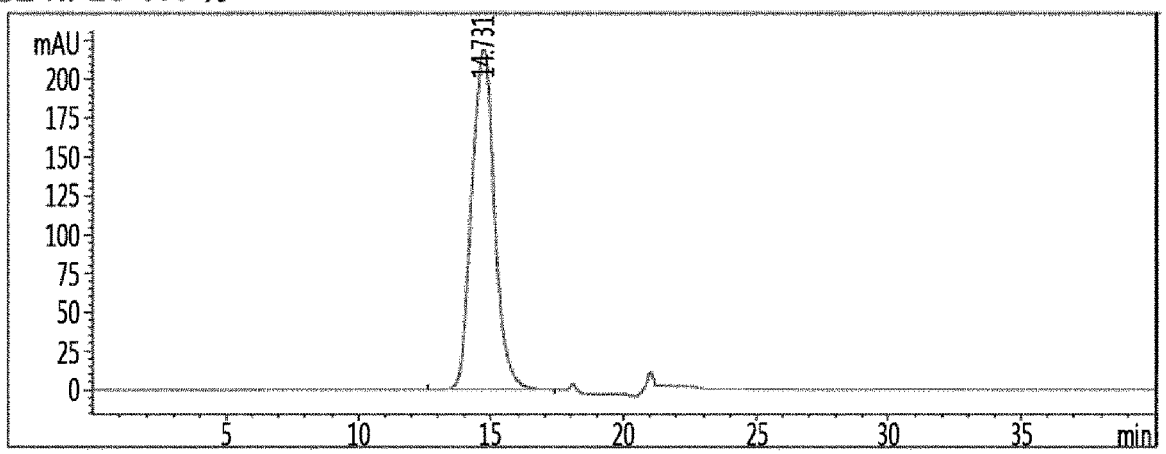

[FIG. 2d]
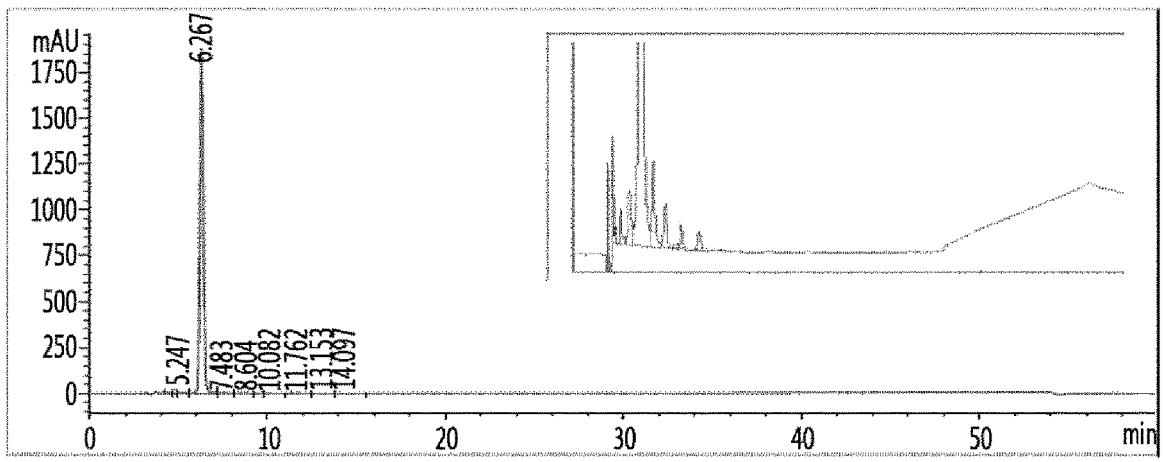
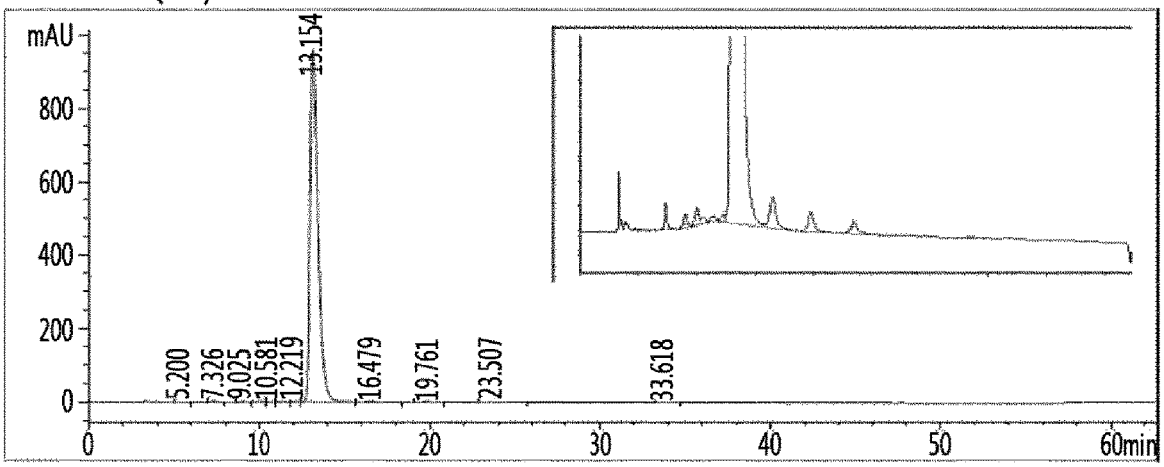
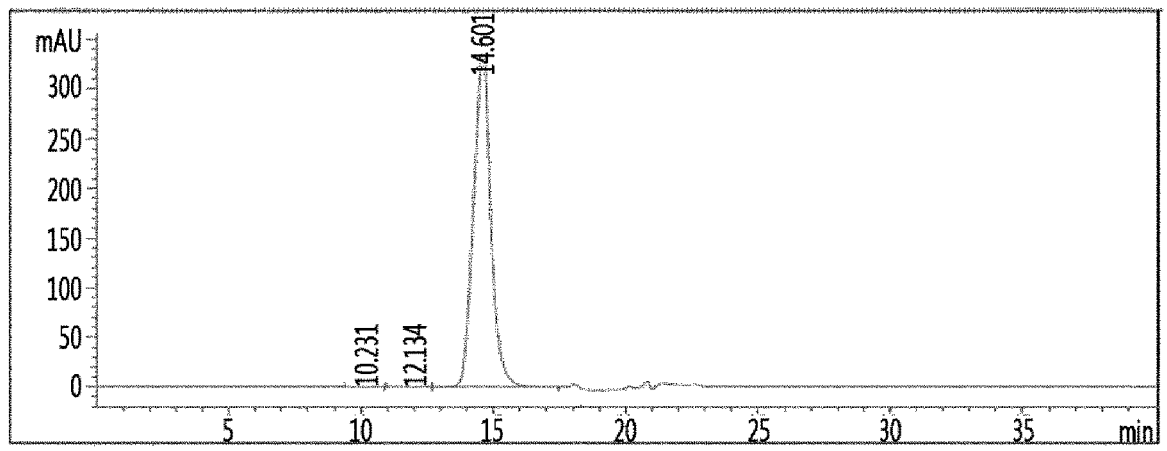

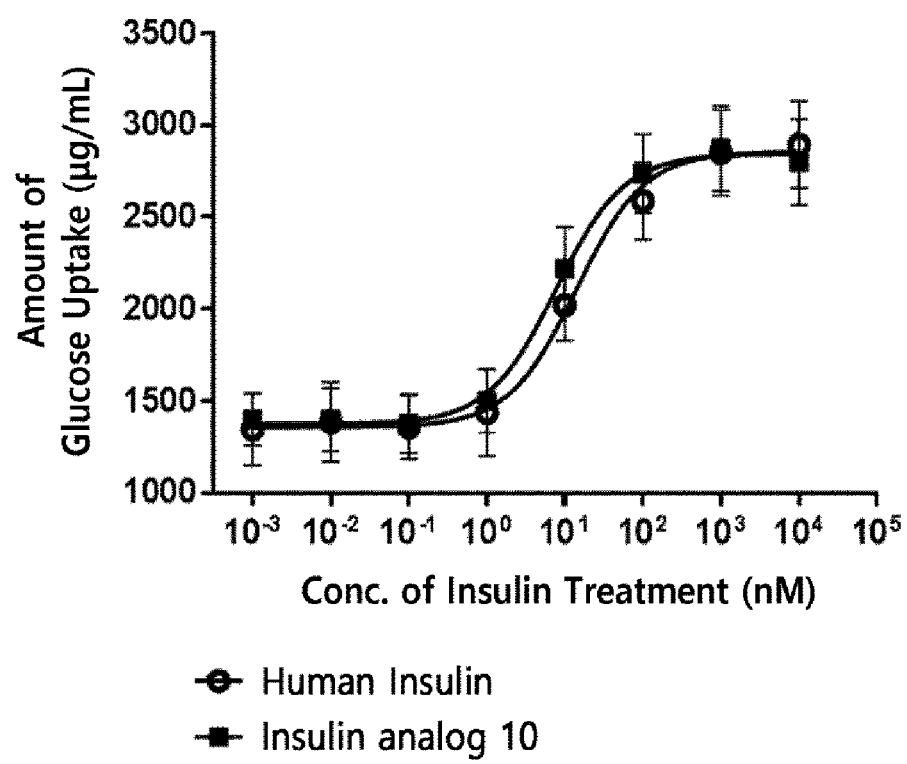
[FIG. 3]

[FIG. 4]
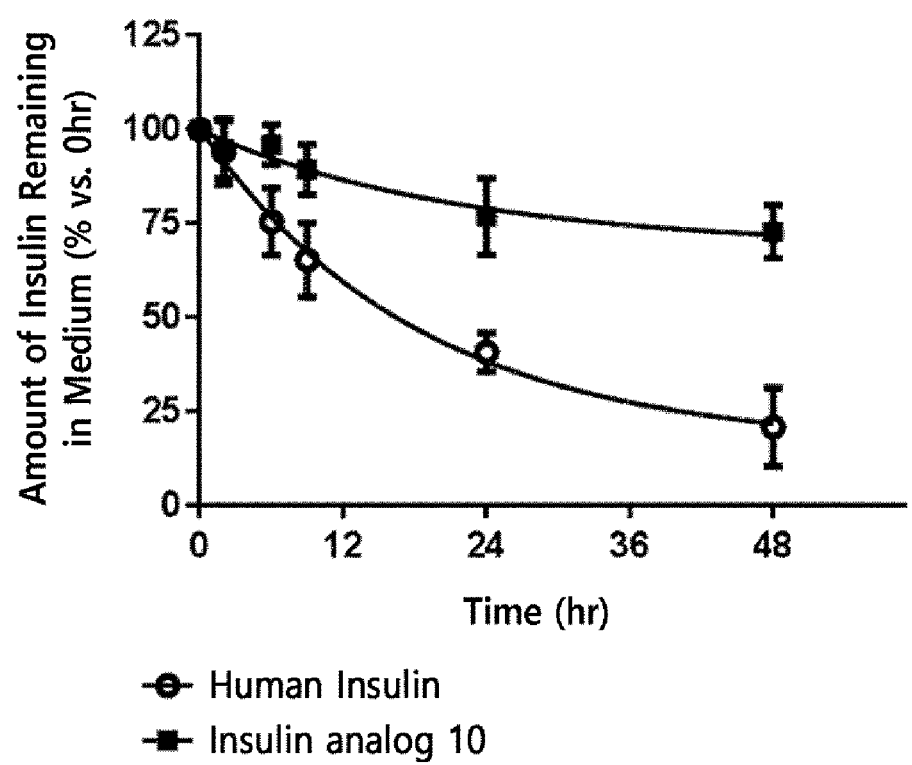

SEQUENCE LISTING

<160> NUMBER OF SEQ ID NOS: 56

<210> SEQ ID NO 1
<211> LENGTH: 34

```
<212> TYPE: DNA
<213> ORGANISM: Artificial Sequence
<220> FEATURE:
<223> OTHER INFORMATION: Primer

<400> SEQUENCE: 1
cagcatctgc tccctccatc agctggagaa ctac                           34

<210> SEQ ID NO 2
<211> LENGTH: 34
<212> TYPE: DNA
<213> ORGANISM: Artificial Sequence
<220> FEATURE:
<223> OTHER INFORMATION: Primer

<400> SEQUENCE: 2
gtagttctcc agctgatgga gggagcagat gctg                           34

<210> SEQ ID NO 3
<211> LENGTH: 34
<212> TYPE: DNA
<213> ORGANISM: Artificial Sequence
<220> FEATURE:
<223> OTHER INFORMATION: Primer

<400> SEQUENCE: 3
cagcatctgc tccctcaagc agctggagaa ctac                           34

<210> SEQ ID NO 4
<211> LENGTH: 34
<212> TYPE: DNA
<213> ORGANISM: Artificial Sequence
<220> FEATURE:
<223> OTHER INFORMATION: Primer

<400> SEQUENCE: 4
gtagttctcc agctgcttga gggagcagat gctg                           34

<210> SEQ ID NO 5
<211> LENGTH: 34
<212> TYPE: DNA
<213> ORGANISM: Artificial Sequence
<220> FEATURE:
<223> OTHER INFORMATION: Primer

<400> SEQUENCE: 5
ctaccagctg gagaacgagt gcaactgagg atcc                           34

<210> SEQ ID NO 6
<211> LENGTH: 34
<212> TYPE: DNA
<213> ORGANISM: Artificial Sequence
<220> FEATURE:
<223> OTHER INFORMATION: Primer

<400> SEQUENCE: 6
ggatcctcag ttgcactcgt tctccagctg gtag                           34

<210> SEQ ID NO 7
<211> LENGTH: 34
<212> TYPE: DNA
<213> ORGANISM: Artificial Sequence
<220> FEATURE:
<223> OTHER INFORMATION: Primer

<400> SEQUENCE: 7
```
ctaccagctg gagaactcct gcaactgagg atcc                34

<210> SEQ ID NO 8
<211> LENGTH: 34
<212> TYPE: DNA
<213> ORGANISM: Artificial Sequence
<220> FEATURE:
<223> OTHER INFORMATION: Primer

<400> SEQUENCE: 8
ggatcctcag ttgcaggagt tctccagctg gtag                34

<210> SEQ ID NO 9
<211> LENGTH: 34
<212> TYPE: DNA
<213> ORGANISM: Artificial Sequence
<220> FEATURE:
<223> OTHER INFORMATION: Primer

<400> SEQUENCE: 9
ctaccagctg gagaacacct gcaactgagg atcc                34

<210> SEQ ID NO 10
<211> LENGTH: 34
<212> TYPE: DNA
<213> ORGANISM: Artificial Sequence
<220> FEATURE:
<223> OTHER INFORMATION: Primer

<400> SEQUENCE: 10
ggatcctcag ttgcaggtgt tctccagctg gtag                34

<210> SEQ ID NO 11
<211> LENGTH: 34
<212> TYPE: DNA
<213> ORGANISM: Artificial Sequence
<220> FEATURE:
<223> OTHER INFORMATION: Primer

<400> SEQUENCE: 11
ctggtggaag ctctcgagct agtgtgcggg gaac                34

<210> SEQ ID NO 12
<211> LENGTH: 34
<212> TYPE: DNA
<213> ORGANISM: Artificial Sequence
<220> FEATURE:
<223> OTHER INFORMATION: Primer

<400> SEQUENCE: 12
gttccccgca cactagctcg agagcttcca ccag                34

<210> SEQ ID NO 13
<211> LENGTH: 34
<212> TYPE: DNA
<213> ORGANISM: Artificial Sequence
<220> FEATURE:
<223> OTHER INFORMATION: Primer

<400> SEQUENCE: 13
ctggtggaag ctctctccct agtgtgcggg gaac                34

<210> SEQ ID NO 14
<211> LENGTH: 34
<212> TYPE: DNA
<213> ORGANISM: Artificial Sequence

```
<220> FEATURE:
<223> OTHER INFORMATION: Primer

<400> SEQUENCE: 14
gttccccgca cactagggag agagcttcca ccag                                34

<210> SEQ ID NO 15
<211> LENGTH: 34
<212> TYPE: DNA
<213> ORGANISM: Artificial Sequence
<220> FEATURE:
<223> OTHER INFORMATION: Primer

<400> SEQUENCE: 15
ctggtggaag ctctcaccct agtgtgcggg gaac                                34

<210> SEQ ID NO 16
<211> LENGTH: 34
<212> TYPE: DNA
<213> ORGANISM: Artificial Sequence
<220> FEATURE:
<223> OTHER INFORMATION: Primer

<400> SEQUENCE: 16
gttccccgca cactagggtg agagcttcca ccag                                34

<210> SEQ ID NO 17
<211> LENGTH: 34
<212> TYPE: DNA
<213> ORGANISM: Artificial Sequence
<220> FEATURE:
<223> OTHER INFORMATION: Primer

<400> SEQUENCE: 17
cagcatctgc tccctcgccc agctggagaa ctac                                34

<210> SEQ ID NO 18
<211> LENGTH: 34
<212> TYPE: DNA
<213> ORGANISM: Artificial Sequence
<220> FEATURE:
<223> OTHER INFORMATION: Primer

<400> SEQUENCE: 18
gtagttctcc agctgggcga gggagcagat gctg                                34

<210> SEQ ID NO 19
<211> LENGTH: 34
<212> TYPE: DNA
<213> ORGANISM: Artificial Sequence
<220> FEATURE:
<223> OTHER INFORMATION: Primer

<400> SEQUENCE: 19
cagcatctgc tccctcgacc agctggagaa ctac                                34

<210> SEQ ID NO 20
<211> LENGTH: 34
<212> TYPE: DNA
<213> ORGANISM: Artificial Sequence
<220> FEATURE:
<223> OTHER INFORMATION: Primer

<400> SEQUENCE: 20
gtagttctcc agctggtcga gggagcagat gctg                                34
```

```
<210> SEQ ID NO 21
<211> LENGTH: 34
<212> TYPE: DNA
<213> ORGANISM: Artificial Sequence
<220> FEATURE:
<223> OTHER INFORMATION: Primer

<400> SEQUENCE: 21
ctggtggaag ctctcgacct agtgtgcggg gaac                              34

<210> SEQ ID NO 22
<211> LENGTH: 34
<212> TYPE: DNA
<213> ORGANISM: Artificial Sequence
<220> FEATURE:
<223> OTHER INFORMATION: Primer

<400> SEQUENCE: 22
gttccccgca cactaggtcg agagcttcca ccag                              34

<210> SEQ ID NO 23
<211> LENGTH: 33
<212> TYPE: DNA
<213> ORGANISM: Artificial Sequence
<220> FEATURE:
<223> OTHER INFORMATION: Primer

<400> SEQUENCE: 23
ggggaacgag gcttcgacta cacccaag acc                                 33

<210> SEQ ID NO 24
<211> LENGTH: 33
<212> TYPE: DNA
<213> ORGANISM: Artificial Sequence
<220> FEATURE:
<223> OTHER INFORMATION: Primer

<400> SEQUENCE: 24
ggtcttgggt gtgtagtcga agcctcgttc ccc                               33

<210> SEQ ID NO 25
<211> LENGTH: 33
<212> TYPE: DNA
<213> ORGANISM: Artificial Sequence
<220> FEATURE:
<223> OTHER INFORMATION: Primer

<400> SEQUENCE: 25
ggggaacgag gcttcgagta cacccaag acc                                 33

<210> SEQ ID NO 26
<211> LENGTH: 33
<212> TYPE: DNA
<213> ORGANISM: Artificial Sequence
<220> FEATURE:
<223> OTHER INFORMATION: Primer

<400> SEQUENCE: 26
ggtcttgggt gtgtactcga agcctcgttc ccc                               33

<210> SEQ ID NO 27
<211> LENGTH: 258
<212> TYPE: DNA
<213> ORGANISM: Artificial Sequence
<220> FEATURE:
<223> OTHER INFORMATION: Analog 1
```

<400> SEQUENCE: 27

```
ttcgttaacc aacacttgtg tggctcacac ctggtggaag ctctctacct agtgtgcggg      60
gaacgaggct tcttctacac acccaagacc cgccgggagg cagaggacct gcaggtgggg     120
caggtggagc tgggcggggg ccctggtgca ggcagcctgc agcccttggc cctggagggg     180
tccctgcaga agcgtggcat tgtggaacaa tgctgtacca gcatctgctc cctccatcag     240
ctggagaact actgcaac                                                   258
```

<210> SEQ ID NO 28
<211> LENGTH: 86
<212> TYPE: PRT
<213> ORGANISM: Artificial Sequence
<220> FEATURE:
<223> OTHER INFORMATION: Analog 1

<400> SEQUENCE: 28

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu His Gln
65                  70                  75                  80

Leu Glu Asn Tyr Cys Asn
                85
```

<210> SEQ ID NO 29
<211> LENGTH: 258
<212> TYPE: DNA
<213> ORGANISM: Artificial Sequence
<220> FEATURE:
<223> OTHER INFORMATION: Analog 2

<400> SEQUENCE: 29

```
ttcgttaacc aacacttgtg tggctcacac ctggtggaag ctctctacct agtgtgcggg      60
gaacgaggct tcttctacac acccaagacc cgccgggagg cagaggacct gcaggtgggg     120
caggtggagc tgggcggggg ccctggtgca ggcagcctgc agcccttggc cctggagggg     180
tccctgcaga agcgtggcat tgtggaacaa tgctgtacca gcatctgctc cctcaagcag     240
ctggagaact actgcaac                                                   258
```

<210> SEQ ID NO 30
<211> LENGTH: 86
<212> TYPE: PRT
<213> ORGANISM: Artificial Sequence
<220> FEATURE:
<223> OTHER INFORMATION: Analog 2

<400> SEQUENCE: 30

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45
```

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Lys Gln
65                  70                  75                  80

Leu Glu Asn Tyr Cys Asn
                85

<210> SEQ ID NO 31
<211> LENGTH: 258
<212> TYPE: DNA
<213> ORGANISM: Artificial Sequence
<220> FEATURE:
<223> OTHER INFORMATION: Analog 3

<400> SEQUENCE: 31
ttcgttaacc aacacttgtg tggctcacac ctggtggaag ctctctacct agtgtgcggg    60
gaacgaggct tcttctacac acccaagacc cgccgggagg cagaggacct gcaggtgggg   120
caggtggagc tgggcggggg ccctggtgca ggcagcctgc agcccttggc cctggagggg   180
tccctgcaga agcgtggcat tgtggaacaa tgctgtacca gcatctgctc cctctaccag   240
ctggagaacg agtgcaac                                                 258

<210> SEQ ID NO 32
<211> LENGTH: 86
<212> TYPE: PRT
<213> ORGANISM: Artificial Sequence
<220> FEATURE:
<223> OTHER INFORMATION: Analog 3

<400> SEQUENCE: 32

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
                20                  25                  30

Glu Ala Glu Asp Leu Gln Val Gly Gln Val Glu Leu Gly Gly Gly Pro
            35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Glu Cys Asn
                85

<210> SEQ ID NO 33
<211> LENGTH: 258
<212> TYPE: DNA
<213> ORGANISM: Artificial Sequence
<220> FEATURE:
<223> OTHER INFORMATION: Analog 4

<400> SEQUENCE: 33
ttcgttaacc aacacttgtg tggctcacac ctggtggaag ctctctacct agtgtgcggg    60
gaacgaggct tcttctacac acccaagacc cgccgggagg cagaggacct gcaggtgggg   120
caggtggagc tgggcggggg ccctggtgca ggcagcctgc agcccttggc cctggagggg   180
tccctgcaga agcgtggcat tgtggaacaa tgctgtacca gcatctgctc cctctaccag   240
ctggagaact cctgcaac                                                 258

<210> SEQ ID NO 34
<211> LENGTH: 86
<212> TYPE: PRT
<213> ORGANISM: Artificial Sequence
<220> FEATURE:
<223> OTHER INFORMATION: Analog 4

<400> SEQUENCE: 34

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Ser Cys Asn
                85
```

<210> SEQ ID NO 35
<211> LENGTH: 258
<212> TYPE: DNA
<213> ORGANISM: Artificial Sequence
<220> FEATURE:
<223> OTHER INFORMATION: Analog 5

<400> SEQUENCE: 35

```
ttcgttaacc aacacttgtg tggctcacac ctggtggaag ctctctacct agtgtgcggg    60
gaacgaggct tcttctacac acccaagacc cgccgggagg cagaggacct gcaggtgggg   120
caggtggagc tgggcggggg ccctggtgca ggcagcctgc agcccttggc cctggagggg   180
tccctgcaga gcgtggcat tgtggaacaa tgctgtacca gcatctgctc cctctaccag   240
ctggagaaca cctgcaac                                                 258
```

<210> SEQ ID NO 36
<211> LENGTH: 86
<212> TYPE: PRT
<213> ORGANISM: Artificial Sequence
<220> FEATURE:
<223> OTHER INFORMATION: Analog 5

<400> SEQUENCE: 36

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Thr Cys Asn
                85
```

<210> SEQ ID NO 37
<211> LENGTH: 258
<212> TYPE: DNA

```
<213> ORGANISM: Artificial Sequence
<220> FEATURE:
<223> OTHER INFORMATION: Analog 6

<400> SEQUENCE: 37
ttcgttaacc aacacttgtg tggctcacac ctggtggaag ctctcgagct agtgtgcggg      60
gaacgaggct tcttctacac acccaagacc cgccgggagg cagaggacct gcaggtgggg     120
caggtggagc tgggcggggg ccctggtgca ggcagcctgc agcccttggc cctggagggg     180
tccctgcaga agcgtggcat tgtggaacaa tgctgtacca gcatctgctc cctctaccag     240
ctggagaact actgcaac                                                   258

<210> SEQ ID NO 38
<211> LENGTH: 86
<212> TYPE: PRT
<213> ORGANISM: Artificial Sequence
<220> FEATURE:
<223> OTHER INFORMATION: Analog 6

<400> SEQUENCE: 38

Phe Val Asn Gln His Leu Cys Gly Ser His Leu Val Glu Ala Leu Glu
1               5                   10                  15

Leu Val Cys Gly Glu Arg Gly Phe Phe Tyr Thr Pro Lys Thr Arg Arg
                20                  25                  30

Glu Ala Glu Asp Leu Gln Val Gly Gln Val Leu Gly Gly Pro
            35                  40                  45

Gly Ala Gly Ser Leu Gln Pro Leu Ala Leu Glu Gly Ser Leu Gln Lys
        50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85

<210> SEQ ID NO 39
<211> LENGTH: 258
<212> TYPE: DNA
<213> ORGANISM: Artificial Sequence
<220> FEATURE:
<223> OTHER INFORMATION: Analog 7

<400> SEQUENCE: 39
ttcgttaacc aacacttgtg tggctcacac ctggtggaag ctctctccct agtgtgcggg      60
gaacgaggct tcttctacac acccaagacc cgccgggagg cagaggacct gcaggtgggg     120
caggtggagc tgggcggggg ccctggtgca ggcagcctgc agcccttggc cctggagggg     180
tccctgcaga agcgtggcat tgtggaacaa tgctgtacca gcatctgctc cctctaccag     240
ctggagaact actgcaac                                                   258

<210> SEQ ID NO 40
<211> LENGTH: 86
<212> TYPE: PRT
<213> ORGANISM: Artificial Sequence
<220> FEATURE:
<223> OTHER INFORMATION: Analog 7

<400> SEQUENCE: 40

Phe Val Asn Gln His Leu Cys Gly Ser His Leu Val Glu Ala Leu Ser
1               5                   10                  15

Leu Val Cys Gly Glu Arg Gly Phe Phe Tyr Thr Pro Lys Thr Arg Arg
                20                  25                  30
```

Glu Ala Glu Asp Leu Gln Val Gly Gln Val Glu Leu Gly Gly Gly Pro
            35                  40                  45

Gly Ala Gly Ser Leu Gln Pro Leu Ala Leu Glu Gly Ser Leu Gln Lys
        50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85

<210> SEQ ID NO 41
<211> LENGTH: 258
<212> TYPE: DNA
<213> ORGANISM: Artificial Sequence
<220> FEATURE:
<223> OTHER INFORMATION: Analog 8

<400> SEQUENCE: 41
ttcgttaacc aacacttgtg tggctcacac ctggtggaag ctctcaccct agtgtgcggg      60
gaacgaggct tcttctacac acccaagacc cgccgggagg cagaggacct gcaggtgggg     120
caggtggagc tgggcggggg ccctggtgca ggcagcctgc agcccttggc cctggagggg     180
tccctgcaga agcgtggcat tgtggaacaa tgctgtacca gcatctgctc cctctaccag     240
ctggagaact actgcaac                                                   258

<210> SEQ ID NO 42
<211> LENGTH: 86
<212> TYPE: PRT
<213> ORGANISM: Artificial Sequence
<220> FEATURE:
<223> OTHER INFORMATION: Analog 8

<400> SEQUENCE: 42

Phe Val Asn Gln His Leu Cys Gly Ser His Leu Val Glu Ala Leu Thr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
            35                  40                  45

Gly Ala Gly Ser Leu Gln Pro Leu Ala Leu Glu Gly Ser Leu Gln Lys
        50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85

<210> SEQ ID NO 43
<211> LENGTH: 258
<212> TYPE: DNA
<213> ORGANISM: Artificial Sequence
<220> FEATURE:
<223> OTHER INFORMATION: Analog 9

<400> SEQUENCE: 43
ttcgttaacc aacacttgtg tggctcacac ctggtggaag ctctctacct agtgtgcggg      60
gaacgaggct tcttctacac acccaagacc cgccgggagg cagaggacct gcaggtgggg     120
caggtggagc tgggcggggg ccctggtgca ggcagcctgc agcccttggc cctggagggg     180
tccctgcaga agcgtggcat tgtggaacaa tgctgtacca gcatctgctc cctcgcccag     240
ctggagaact actgcaac                                               258

<210> SEQ ID NO 44
<211> LENGTH: 86
<212> TYPE: PRT
<213> ORGANISM: Artificial Sequence
<220> FEATURE:
<223> OTHER INFORMATION: Analog 9

<400> SEQUENCE: 44

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
                20                  25                  30

Glu Ala Glu Asp Leu Gln Val Gly Gln Val Glu Leu Gly Gly Gly Pro
            35                  40                  45

Gly Ala Gly Ser Leu Gln Pro Leu Ala Leu Glu Gly Ser Leu Gln Lys
        50                  55                  60

Arg Gly Ile Val Glu Gln Cys Cys Thr Ser Ile Cys Ser Leu Ala Gln
65                  70                  75                  80

Leu Glu Asn Tyr Cys Asn
                85

<210> SEQ ID NO 45
<211> LENGTH: 258
<212> TYPE: DNA
<213> ORGANISM: Artificial Sequence
<220> FEATURE:
<223> OTHER INFORMATION: Analog 10

<400> SEQUENCE: 45
ttcgttaacc aacacttgtg tggctcacac ctggtggaag ctctctacct agtgtgcggg      60
gaacgaggct tcttctacac acccaagacc cgccgggagg cagaggacct gcaggtgggg     120
caggtggagc tgggcggggg ccctggtgca ggcagcctgc agcccttggc cctggagggg     180
tccctgcaga agcgtggcat tgtggaacaa tgctgtacca gcatctgctc cctcgaccag     240
ctggagaact actgcaac                                                  258

<210> SEQ ID NO 46
<211> LENGTH: 86
<212> TYPE: PRT
<213> ORGANISM: Artificial Sequence
<220> FEATURE:
<223> OTHER INFORMATION: Analog 10

<400> SEQUENCE: 46

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
                20                  25                  30

Glu Ala Glu Asp Leu Gln Val Gly Gln Val Glu Leu Gly Gly Gly Pro
            35                  40                  45

Gly Ala Gly Ser Leu Gln Pro Leu Ala Leu Glu Gly Ser Leu Gln Lys
        50                  55                  60

Arg Gly Ile Val Glu Gln Cys Cys Thr Ser Ile Cys Ser Leu Asp Gln
65                  70                  75                  80

Leu Glu Asn Tyr Cys Asn
                85

<210> SEQ ID NO 47
<211> LENGTH: 258
<212> TYPE: DNA
<213> ORGANISM: Artificial Sequence
<220> FEATURE:
<223> OTHER INFORMATION: Analog 11

<400> SEQUENCE: 47

```
ttcgttaacc aacacttgtg tggctcacac ctggtggaag ctctcgacct agtgtgcggg      60
gaacgaggct tcttctacac acccaagacc cgccggagg cagaggacct gcaggtgggg     120
caggtggagc tgggcggggg ccctggtgca ggcagcctgc agcccttggc cctggagggg    180
tccctgcaga agcgtggcat tgtggaacaa tgctgtacca gcatctgctc cctctaccag    240
ctggagaact actgcaac                                                  258
```

<210> SEQ ID NO 48
<211> LENGTH: 86
<212> TYPE: PRT
<213> ORGANISM: Artificial Sequence
<220> FEATURE:
<223> OTHER INFORMATION: Analog 11

<400> SEQUENCE: 48

```
Phe Val Asn Gln His Leu Cys Gly Ser His Leu Val Glu Ala Leu Asp
1               5                  10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85
```

<210> SEQ ID NO 49
<211> LENGTH: 258
<212> TYPE: DNA
<213> ORGANISM: Artificial Sequence
<220> FEATURE:
<223> OTHER INFORMATION: Analog 12

<400> SEQUENCE: 49

```
ttcgttaacc aacacttgtg tggctcacac ctggtggaag ctctctacct agtgtgcggg      60
gaacgaggct tcgactacac acccaagacc cgccggagg cagaggacct gcaggtgggg     120
caggtggagc tgggcggggg ccctggtgca ggcagcctgc agcccttggc cctggagggg    180
tccctgcaga agcgtggcat tgtggaacaa tgctgtacca gcatctgctc cctctaccag    240
ctggagaact actgcaac                                                  258
```

<210> SEQ ID NO 50
<211> LENGTH: 86
<212> TYPE: PRT
<213> ORGANISM: Artificial Sequence
<220> FEATURE:
<223> OTHER INFORMATION: Analog 12

<400> SEQUENCE: 50

```
Phe Val Asn Gln His Leu Cys Gly Ser His Leu Val Glu Ala Leu Tyr
1               5                  10                  15
```

Leu Val Cys Gly Glu Arg Gly Phe Asp Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn
            85

<210> SEQ ID NO 51
<211> LENGTH: 258
<212> TYPE: DNA
<213> ORGANISM: Artificial Sequence
<220> FEATURE:
<223> OTHER INFORMATION: Analog 13

<400> SEQUENCE: 51
ttcgttaacc aaacacttgtg tggctcacac ctggtggaag ctctctacct agtgtgcggg      60
gaacgaggct tcgagtacac acccaagacc cgccggagg cagaggacct gcaggtgggg      120
caggtggagc tgggcggggg ccctggtgca ggcagcctgc agcccttggc cctggagggg     180
tccctgcaga agcgtggcat tgtgaacaa tgctgtacca gcatctgctc cctctaccag      240
ctggagaact actgcaac                                                 258

<210> SEQ ID NO 52
<211> LENGTH: 86
<212> TYPE: PRT
<213> ORGANISM: Artificial Sequence
<220> FEATURE:
<223> OTHER INFORMATION: Analog 13

<400> SEQUENCE: 52

Phe Val Asn Gln His Leu Cys Gly Ser His Leu Val Glu Ala Leu Tyr
1               5                   10                  15

Leu Val Cys Gly Glu Arg Gly Phe Glu Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn
            85

<210> SEQ ID NO 53
<211> LENGTH: 21
<212> TYPE: PRT
<213> ORGANISM: Homo sapiens

<400> SEQUENCE: 53

Gly Ile Val Glu Gln Cys Cys Thr Ser Ile Cys Ser Leu Tyr Gln Leu
1               5                   10                  15

Glu Asn Tyr Cys Asn
            20

-continued

```
<210> SEQ ID NO 54
<211> LENGTH: 30
<212> TYPE: PRT
<213> ORGANISM: Homo sapiens

<400> SEQUENCE: 54

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 55
<211> LENGTH: 21
<212> TYPE: PRT
<213> ORGANISM: Artificial Sequence
<220> FEATURE:
<223> OTHER INFORMATION: Insulin analog, A-chain
<220> FEATURE:
<221> NAME/KEY: MISC_FEATURE
<222> LOCATION: (1)
<223> OTHER INFORMATION: Xaa is alanine, glycine, glutamine, histidine,
      glutamic acid, or asparagine
<220> FEATURE:
<221> NAME/KEY: MISC_FEATURE
<222> LOCATION: (5)
<223> OTHER INFORMATION: Xaa is alanine, glutamic acid, glutamine,
      histidine, or asparagine
<220> FEATURE:
<221> NAME/KEY: MISC_FEATURE
<222> LOCATION: (12)
<223> OTHER INFORMATION: Xaa is alanine, serine, glutamine, glutamic
      acid, histidine, or asparagine
<220> FEATURE:
<221> NAME/KEY: MISC_FEATURE
<222> LOCATION: (14)
<223> OTHER INFORMATION: Xaa is tyrosine, histidine, lysine, alanine, or
      aspartic acid
<220> FEATURE:
<221> NAME/KEY: MISC_FEATURE
<222> LOCATION: (16)
<223> OTHER INFORMATION: Xaa is alanine, leucine, tyrosine, histidine,
      glutamic acid, or asparagine
<220> FEATURE:
<221> NAME/KEY: MISC_FEATURE
<222> LOCATION: (19)
<223> OTHER INFORMATION: Xaa is tyrosine, glutamic acid, serine, or
      threonine
<220> FEATURE:
<221> NAME/KEY: MISC_FEATURE
<222> LOCATION: (21)
<223> OTHER INFORMATION: Xaa is asparagine, glycine, histidine, or
      alanine

<400> SEQUENCE: 55

Xaa Ile Val Glu Xaa Cys Cys Thr Ser Ile Cys Xaa Leu Xaa Gln Xaa
1               5                   10                  15

Glu Asn Xaa Cys Xaa
            20

<210> SEQ ID NO 56
<211> LENGTH: 30
<212> TYPE: PRT
<213> ORGANISM: Artificial Sequence
<220> FEATURE:
<223> OTHER INFORMATION: Insulin analog, B-chain
<220> FEATURE:
<221> NAME/KEY: MISC_FEATURE
<222> LOCATION: (16)
<223> OTHER INFORMATION: Xaa is tyrosine, glutamic acid, serine,
      threonine, or aspartic acid
<220> FEATURE:
<221> NAME/KEY: MISC_FEATURE
<222> LOCATION: (25)
```

```
<223> OTHER INFORMATION: Xaa is phenylalanine, aspartic acid, or
      glutamic acid
<220> FEATURE:
<221> NAME/KEY: MISC_FEATURE
<222> LOCATION: (27)
<223> OTHER INFORMATION: Xaa is threonine, or is absent
<220> FEATURE:
<221> NAME/KEY: MISC_FEATURE
<222> LOCATION: (28)
<223> OTHER INFORMATION: Xaa is proline, glutamic acid, or aspartic
      acid, or is absent

<400> SEQUENCE: 56

Phe Val Asn Gln His Leu Cys Gly Ser His Leu Val Glu Ala Leu Xaa
1               5                   10                  15

Leu Val Cys Gly Glu Arg Gly Phe Xaa Tyr Xaa Xaa Lys Thr
            20                  25              30
```

INSULIN ANALOGS WITH REDUCED AFFINITY TO INSULIN RECEPTOR AND USE THEREOF

CROSS REFERENCE TO RELATED APPLICATIONS

This application is a National Stage of International Application No. PCT/KR2017/010504 filed Sep. 22, 2017, claiming priority based on Korean Patent Application No. 10-2016-0122484 filed Sep. 23, 2016.

TECHNICAL FIELD

The present invention relates to a novel insulin analog, a use thereof, and a method of preparing the analog.

BACKGROUND ART

It is known that proteins in the body are removed by various routes including decomposition by proteases in the blood, excretion through the kidney, removal by receptors, etc. In this regard, various attempts have been made to improve therapeutic effects of proteins via increase of the half-life of physiological proteins by avoiding protein scavenging mechanisms.

Generally, insulin is a hormone secreted by the pancreas of the human body which regulates blood glucose levels and has the role of maintaining normal blood glucose levels while carrying surplus glucose in the blood to cells to provide energy for cells. In diabetic patients, however, insulin does not function properly due to lack of insulin, resistance to insulin, and loss of beta-cell function, and thus glucose in the blood cannot be utilized as an energy source and the blood glucose level is elevated, leading to hyperglycemia. As a result, diabetic patients cannot utilize the glucose in the blood as an energy source, but show symptoms of hyperglycemia with a high glucose level and excrete the glucose in the urine, which becomes the cause of various complications. Accordingly, insulin therapy is essential for patients with abnormal insulin secretion (type I) or insulin resistance (type II), and blood glucose levels can be normally regulated by insulin administration.

However, like other protein and peptide hormones, insulin has a very short in-vivo half-life, and thus has a disadvantage of repeated administration. Such frequent administration causes severe pain and discomfort for the patients and thus there is a need to improve the administration from the aspects of patient compliance, safety, and convenience.

Accordingly, studies have focused on the development of various protein formulations, chemical conjugates (e.g., fatty acid conjugate), etc. for improving the therapeutic effects as well as the quality of patients' lives by reducing the frequency of administration through the increase of the in-vivo half-life of these protein drugs such as insulin.

According to a previous report, 50% or more of insulin is removed in the kidneys and the rest is removed via a receptor mediated clearance (RMC) process in target sites such as muscle, fat, liver, etc.

In this regard, there were reports (*J Pharmacol Exp Ther* (1998) 286: 959, Diabetes Care (1990) 13: 923, and *Diabetes* (1990) 39: 1033, etc.) that in-vitro activity is reduced to avoid RMC of insulin, thereby increasing the insulin level in the blood. However, in *J Pharmacol Exp Ther* (1998) 286: 959, *Diabetes Care* (1990) 13: 923, the insulin analogs suggested therein had substitutions of at least two amino acids or no specific result was provided, whereas, in *Diabetes* (1990) 39: 1033, the insulin analogs showed no change in their binding affinity to receptors or their activities were reduced by substituting the amino acids which were directly involved in binding to insulin receptors.

The present inventors have developed those analogs which can reduce only the binding affinity to insulin receptors by substituting the amino acids which are not directly involved in the binding to insulin receptors, and have confirmed that they reduced binding affinity to insulin receptors, thereby completing the present invention.

DISCLOSURE

Technical Problem

An object of the present invention is to provide a novel insulin analog.

Another object of the present invention is to provide an isolated nucleic acid encoding the insulin analog, a recombinant expression vector including the nucleic acid, and a transformant including the expression vector.

Still another object of the present invention is to provide a method for preparing the insulin analog.

Still another object of the present invention is to provide a composition containing the insulin analog as an active ingredient, e.g., a pharmaceutical composition.

Still another object of the present invention is to provide a pharmaceutical composition for treating insulin-related diseases (e.g., diabetes) containing the insulin analog as an active ingredient.

Still another object of the present invention is to provide a method for treating diabetes, including administering the insulin analog or a pharmaceutical composition containing the insulin analog as an active ingredient to a subject in need thereof.

Still another object of the present invention is to provide a use of the insulin analog in the preparation of a medicament.

Still another object of the present invention is to provide a use of the insulin analog in the treatment of insulin-related diseases, specifically diabetes.

Technical Solution

In order to achieve the above objects, an aspect of the present invention provides an insulin analog, and specifically an insulin analog which includes at least one modification in amino acid(s) selected from the group consisting of the $16^{th}$ amino acid of the B-chain, the $25^{th}$ amino acid of the B-chain, the $14^{th}$ amino acid of the A-chain, and the $19^{th}$ amino acid of the A-chain of native insulin.

In an exemplary embodiment, the modification may be a modification of the $16^{th}$ amino acid of the B-chain of native insulin (i.e., tyrosine) into glutamic acid, serine, threonine, or aspartic acid; a modification of the $25^{th}$ amino acid of the B-chain of native insulin (i.e., phenylalanine) into aspartic acid or glutamic acid; a modification of the $14^{th}$ amino acid of the A-chain of native insulin (i.e., tyrosine) into histidine, lysine, alanine, or aspartic acid; or a modification of the $19^{th}$ amino acid of the A-chain of native insulin (i.e., tyrosine) into glutamic acid, serine, or threonine.

In another exemplary embodiment, the insulin analog may be an insulin analog which includes all of the combinations of the A-chain of SEQ ID NO: 55 represented by General Formula 1 below and the B-chain of SEQ ID NO: 56 represented by General Formula 2 below, excluding native insulin, i.e., excluding the peptide in which the A-chain coincides with SEQ ID NO: 53 while the B-chain also coincides with SEQ ID NO: 54.

Xaa1-Ile-Val-Glu-Xaa5-Cys-Cys-Thr-Ser-Ile-Cys-
Xaa12-Leu-Xaa14-Gln-Xaa16-Glu-Asn-Xaa19-
Cys-Xaa21 (SEQ ID NO: 55)  [General Formula 1]

In General Formula 1,

Xaa1 is alanine, glycine, glutamine, histidine, glutamic acid, or asparagine,

Xaa5 is alanine, glutamic acid, glutamine, histidine, or asparagine,

Xaa12 is alanine, serine, glutamine, glutamic acid, histidine, or asparagine,

Xaa14 is tyrosine, histidine, lysine, alanine, or aspartic acid,

Xaa16 is alanine, leucine, tyrosine, histidine, glutamic acid, or asparagine,

Xaa19 is tyrosine, glutamic acid, serine, or threonine, and

Xaa21 is asparagine, glycine, histidine, or alanine.

Phe-Val-Asn-Gln-His-Leu-Cys-Gly-Ser-His-Leu-Val-
Glu-Ala-Leu-Xaa16-Leu-Val-Cys-Gly-Glu-Arg-
Gly-Phe-Xaa25-Tyr-Xaa27-Xaa28-Lys-Thr
(SEQ ID NO: 56)  [General Formula 2]

In General Formula 2,

Xaa16 is tyrosine, glutamic acid, serine, threonine, or aspartic acid,

Xaa25 is phenylalanine, aspartic acid, or glutamic acid,

Xaa27 is threonine, or is absent, and

Xaa28 is proline, glutamic acid, or aspartic acid, or is absent.

In still another exemplary embodiment, the insulin analog may be an insulin analog which includes the A-chain of SEQ ID NO: 55 represented by General Formula 1 above and the B-chain of SEQ ID NO: 54.

In still another exemplary embodiment, the insulin analog may be an insulin analog which includes the A-chain of SEQ ID NO: 53 and the B-chain of SEQ ID NO: 56 represented by General Formula 2 above.

In still another exemplary embodiment, the insulin analog may be an insulin analog, wherein:

in General Formula 1, Xaa1 is glycine, Xaa5 is glutamine, Xaa12 is serine, Xaa14 is tyrosine, histidine, lysine, alanine, or aspartic acid, Xaa16 is leucine, Xaa19 is tyrosine, glutamic acid, serine, or threonine, and Xaa21 is asparagine; and in General Formula 2, Xaa16 is tyrosine, glutamic acid, serine, threonine, or aspartic acid, Xaa25 is phenylalanine, aspartic acid, or glutamic acid, Xaa27 is threonine, and Xaa28 is proline.

In still another exemplary embodiment, the insulin analog may be an insulin analog, wherein:

in General Formula 1,

Xaa1 is glycine, Xaa5 is glutamine, Xaa12 is serine, Xaa14 is tyrosine, Xaa16 is leucine, Xaa19 is tyrosine, glutamic acid, or serine, and Xaa21 is asparagine; and in General Formula 2, Xaa16 is tyrosine, glutamic acid, serine, or aspartic acid, Xaa25 is phenylalanine, aspartic acid, or glutamic acid, Xaa27 is threonine, and Xaa28 is proline.

In still another exemplary embodiment, the insulin analog may be an insulin analog, wherein:

(1) in General Formula 1, Xaa1 is glycine, Xaa5 is glutamine, Xaa12 is serine, Xaa14 is histidine, Xaa16 is leucine, Xaa19 is tyrosine, and Xaa21 is asparagine; and in General Formula 2, Xaa16 is tyrosine, Xaa25 is phenylalanine, Xaa27 is threonine, Xaa28 is proline;

(2) in General Formula 1, Xaa1 is glycine, Xaa5 is glutamine, Xaa12 is serine, Xaa14 is lysine, Xaa16 is leucine, Xaa19 is tyrosine, and Xaa21 is asparagine; and in General Formula 2, Xaa16 is tyrosine, Xaa25 is phenylalanine, Xaa27 is threonine, and Xaa28 is proline;

(3) in General Formula 1, Xaa1 is glycine, Xaa5 is glutamine, Xaa12 is serine, Xaa14 is tyrosine, Xaa16 is leucine, Xaa19 is glutamic acid, and Xaa21 is asparagine; and, in General Formula 2, Xaa16 is tyrosine, Xaa25 is phenylalanine, Xaa27 is threonine, and Xaa28 is proline;

(4) in General Formula 1, Xaa1 is glycine, Xaa5 is glutamine, Xaa12 is serine, Xaa14 is tyrosine, Xaa16 is leucine, Xaa19 is serine, and Xaa21 is asparagine; and in General Formula 2, Xaa16 is tyrosine, Xaa25 is phenylalanine, Xaa27 is threonine, and Xaa28 is proline;

(5) in General Formula 1, Xaa1 is glycine, Xaa5 is glutamine, Xaa12 is serine, Xaa14 is tyrosine, Xaa16 is leucine, Xaa19 is threonine, and Xaa21 is asparagine; and in General Formula 2, Xaa16 is tyrosine, Xaa25 is phenylalanine, Xaa27 is threonine, and Xaa28 is proline;

(6) in General Formula 1, Xaa1 is glycine, Xaa5 is glutamine, Xaa12 is serine, Xaa14 is tyrosine, Xaa16 is leucine, Xaa19 is tyrosine, and Xaa21 is asparagine; and in General Formula 2, Xaa16 is glutamic acid, Xaa25 is phenylalanine, Xaa27 is threonine, and Xaa28 is proline;

(7) in General Formula 1, Xaa1 is glycine, Xaa5 is glutamine, Xaa12 is serine, Xaa14 is tyrosine, Xaa16 is leucine, Xaa19 is tyrosine, and Xaa21 is asparagine; and in General Formula 2, Xaa16 is serine, Xaa25 is phenylalanine, Xaa27 is threonine, and Xaa28 is proline;

(8) in General Formula 1, Xaa1 is glycine, Xaa5 is glutamine, Xaa12 is serine, Xaa14 is tyrosine, Xaa16 is leucine, Xaa19 is tyrosine, and Xaa21 is asparagine; and, in General Formula 2, Xaa16 is threonine, Xaa25 is phenylalanine, Xaa27 is threonine, and Xaa28 is proline;

(9) in General Formula 1, Xaa1 is glycine, Xaa5 is glutamine, Xaa12 is serine, Xaa14 is alanine, Xaa16 is leucine, Xaa19 is tyrosine, and Xaa21 is asparagine; and in General Formula 2, Xaa16 is tyrosine, Xaa25 is phenylalanine, Xaa27 is threonine, and Xaa28 is proline;

(10) in General Formula 1, Xaa1 is glycine, Xaa5 is glutamine, Xaa12 is serine, Xaa14 is aspartic acid, Xaa16 is leucine, Xaa19 is tyrosine, and Xaa21 is asparagine; and in General Formula 2, Xaa16 is tyrosine, Xaa25 is phenylalanine, Xaa27 is threonine, and Xaa28 is proline;

(11) in General Formula 1, Xaa1 is glycine, Xaa5 is glutamine, Xaa12 is serine, Xaa14 is tyrosine, Xaa16 is leucine, Xaa19 is tyrosine, and Xaa21 is asparagine; and in General Formula 2, Xaa16 is aspartic acid, Xaa25 is phenylalanine, Xaa27 is threonine, and Xaa28 is proline;

(12) in General Formula 1, Xaa1 is glycine, Xaa5 is glutamine, Xaa12 is serine, Xaa14 is tyrosine, Xaa16 is leucine, Xaa19 is tyrosine, and Xaa21 is asparagine; and in General Formula 2, Xaa16 is tyrosine, Xaa25 is aspartic acid, Xaa27 is threonine, and Xaa28 is proline; and

(13) in General Formula 1, Xaa1 is glycine, Xaa5 is glutamine, Xaa12 is serine, Xaa14 is tyrosine, Xaa16 is leucine, Xaa19 is tyrosine, and Xaa21 is asparagine; and in General Formula 2, Xaa16 is tyrosine, Xaa25 is glutamic acid, Xaa27 is threonine, and Xaa28 is proline.

In still another exemplary embodiment, the insulin analog may be an insulin analog including an amino acid sequence selected from the group consisting of SEQ ID NOS: 28, 30, 32, 34, 36, 38, 40, 42, 44, 46, 48, 50, and 52.

In still another aspect, the present invention provides an isolated nucleic acid encoding the insulin analog.

In still another aspect, the present invention provides a recombinant expression vector including the nucleic acid.

In still another aspect, the present invention provides a transformant including the recombinant expression vector.

In an exemplary embodiment, the transformant may be *E. coli*.

In still another aspect, the present invention provides a method of preparing the insulin analog, including:
  a) expressing an insulin analog by culturing a transformant including the nucleic acid encoding the insulin analog; and
  b) isolating and purifying the expressed insulin analog.

In an exemplary embodiment, the isolating and purifying may include:
  b-1) obtaining the transformant from the culture in step a) and pulverizing the same;
  b-2) recovering the expressed insulin analog from the pulverized cell lysate followed by refolding the same;
  b-3) purifying the refolded insulin analog by cation exchange chromatography;
  b-4) treating the purified insulin analog with trypsin and carboxypeptidase B; and
  b-5) sequentially purifying the treated insulin analog by cation exchange chromatography, and anion exchange chromatography or reversed-phase chromatography.

In still another aspect, the present invention provides a composition containing the insulin analog as an active ingredient, e.g., a pharmaceutical composition.

In still another aspect, the present invention provides a pharmaceutical composition for treating insulin-related diseases (e.g., diabetes) containing the insulin analog as an active ingredient.

In still another aspect, the present invention provides a method for treating insulin-related diseases (e.g., diabetes), including administering the insulin analog or a pharmaceutical composition containing the insulin analog as an active ingredient to a subject in need thereof.

In still another aspect, the present invention provides a use of the insulin analog in the preparation of a medicament.

In an embodiment, the medicament is for preventing or treating insulin-related diseases.

In another embodiment, the medicament is for preventing or treating diabetes.

In still another aspect, the present invention provides a use of the insulin analog in the treatment of insulin-related diseases, specifically diabetes.

Advantageous Effects of the Invention

The non-native insulin analog of the present invention can improve compliance of patients in need of insulin administration.

BRIEF DESCRIPTIONS OF THE DRAWINGS

FIG. 1 shows the analysis results of purity of insulin analogs by protein electrophoresis, and specifically, the results of representative insulin Analogs 9, 10, 11, and 12 (lane 1: size marker; lane 2: native insulin; lane 3: insulin Analog 9; lane 4: insulin Analog 10; lane 5: insulin Analog 11; and lane 6: insulin Analog 12).

FIGS. 2a to 2d show the analysis results of the purity of insulin analogs by high-pressure chromatography, and specifically, the results of representative insulin analogs 9, 10, 11, and 12. In each drawing, the results of RP-HPLC (C18), RP-HPLC (C4), and SE-HPLC are shown in order from top to bottom.

FIG. 3 shows experimental results confirming glucose uptake ability of human insulin and insulin Analog 10.

FIG. 4 shows experimental results confirming the cell stability of human insulin and insulin Analog 10.

DETAILED DESCRIPTION OF THE INVENTION

Hereinbelow, exemplary embodiments of the present invention will be described in detail.

Meanwhile, each of the explanations and exemplary embodiments disclosed herein can be applied to other explanations and exemplary embodiments. That is, all combinations of various factors disclosed herein belong to the scope of the present invention. Furthermore, the scope of the present invention should not be limited by the specific disclosure provided hereinbelow.

Additionally, those skilled in the art will be able to recognize or confirm, based on routine experimentation, many equivalents to the specific embodiments of the present invention described in this application, and such equivalents are intended to be included in the present invention.

Through the entire specification, the conventional 1-letter and 3-letter codes for the amino acids are used. Additionally, the amino acids mentioned in abbreviations herein are described according to the IUPAC-IUB rules.

An aspect of the present invention provides a novel insulin analog, and specifically, an insulin analog which includes at least one modification in amino acid(s) selected from the group consisting of the $16^{th}$ amino acid of the B-chain, the $25^{th}$ amino acid of the B-chain, the $14^{th}$ amino acid of the A-chain, and the $19^{th}$ amino acid of the A-chain of native insulin.

As used herein, the term "insulin analog" refers to non-native insulin which is different from native insulin.

The insulin analog includes non-native human insulin which is different from native human insulin. Such an insulin analog includes analogs in which a part of the amino acid of native insulin is modified by addition, deletion, or substitution.

Specifically, the insulin analog of the present invention may be one which has a sequence identify of at least 60%, at least 65%, at least 70%, at least 75%, at least 80%, at least 85%, at least 90%, at least 91%, at least 92%, at least 93%, at least 94%, or at least 95%, comparing its sequence identity to that of native insulin sequence. Additionally, the insulin analog of the present invention may be one which has a reduced receptor binding affinity compared to that of native insulin while having the above sequence identity. Additionally, the insulin analog may have a glucose uptake ability as in native insulin and/or have an ability to lower the in-vivo blood glucose levels.

More specifically, the insulin analog of the present invention may exhibit a binding affinity to insulin receptors of about 99% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 9% or less, about 8% or less, about 7% or less, about 6% or less, about 5% or less, about 4% or less, about 3% or less, about 2% or less, about 1% or less, or about 0.1% or less, compared to the binding affinity of native insulin to insulin receptors (100%) (however, the binding affinity of the insulin analog of the present invention to insulin receptors does not correspond to 0%).

The binding affinity of insulin analogs to insulin receptors may be evaluated by Scintillation proximity assay (SPA), which utilizes the competitive reaction between an insulin analog and I$^{125}$-tagged insulin in a cell membrane which overexpresses recombinant human insulin receptors. This method can also be used for the evaluation of binding affinity of insulin analogs to insulin receptors. As an exemplary embodiment of the method, the method used in Example 8 may be used.

As used herein, the term "about" refers to a range including ±0.5, ±0.4, ±0.3, ±0.2, ±0.1, etc., and the term "about" includes any numerical value that is equivalent or in the range being similar to the numerical value following the term, but is not limited to.

Additionally, the insulin analog of the present invention may have glucose uptake ability as in native insulin.

Specifically, the insulin analog of the present invention may be one which has glucose uptake ability of about 10% or more, about 20% or more, about 30% or more, about 40% or more, about 50% or more, about 55% or more, about 60% or more, about 65% or more, about 70% or more, about 75% or more, about 80% or more, about 85% or more, about 90% or more, about 95% or more, about 100% or more, about 110% or more, about 120% or more, about 130% or more, about 140% or more, about 150% or more, about 160% or more, about 170% or more, about 180% or more, about 190% or more, or about 200% or more, compared to the glucose uptake ability of native insulin (100%).

The measurement of glucose uptake ability can be achieved by various methods for measuring glucose uptake ability known in the art, and for example, can be achieved by the method for measuring glucose uptake ability described in Example 9, but the measurement method is not limited thereto.

Specifically, the insulin analogs to be applied in the present invention may be in the form of a single polypeptide chain or two polypeptide chains, more preferably two polypeptide chain, but the insulin analogs are not particularly limited thereto.

The insulin analog in the form of two polypeptide chains may be composed of two polypeptides, i.e., a polypeptide corresponding to the A-chain of native insulin and a polypeptide corresponding to the B-chain of native insulin. In particular, corresponding to the A-chain or B-chain of native insulin may refer to cases in which any one chain of the polypeptides of the two polypeptide chains has a sequence identify of at least 60%, at least 65%, at least 70%, at least 75%, at least 80%, at least 85%, at least 90%, at least 91%, at least 92%, at least 93%, at least 94%, or at least 95%, compared to that of the A-chain or B-chain of native insulin, but is not particularly limited thereto, and those skilled in the art can easily determine the same by comparison between the sequence constituting the two polypeptide chains and that of the A-chain or B-chain of native insulin.

Native insulin is a hormone secreted by the pancreas and generally have the role of promoting intracellular glucose absorption and inhibiting fat breakdown, thereby controlling in-vivo blood glucose levels. Insulin, which can control blood glucose levels, is generated from the processing of its precursor, proinsulin, which does not have the function of controlling blood glucose levels. Insulin is composed of two polypeptide chains, i.e., the A-chain and the B-chain, which include 21 and 30 amino acids, respectively, and are interlinked by two disulfide bridges. Each of the A-chain and the B-chain may include the amino acid sequences represented by SEQ ID NOS: 53 and 54 shown below.

A-chain:
(SEQ ID NO: 53)
Gly-Ile-Val-Glu-Gln-Cys-Cys-Thr-Ser-Ile-Cys-Ser-
Leu-Tyr-Gln-Leu-Glu-Asn-Tyr-Cys-Asn B-chain:
(SEQ ID NO: 54)
Phe-Val-Asn-Gln-His-Leu-Cys-Gly-Ser-His-Leu-Val-
Glu-Ala-Leu-Tyr-Leu-Val-Cys-Gly-Glu-Arg-Gly-Phe-
Phe-Tyr-Thr-Pro-Lys-Thr In an exemplary embodiment, the insulin analogs described in the present invention may be those with a reduced binding affinity to receptors while having the function of controlling the in-vivo blood glucose levels like the native insulin. More specifically, the insulin analog may possess the ability of lowering in-vivo blood glucose levels.

Additionally, in an exemplary embodiment, the kind and size of the insulin analogs may not be particularly limited as long as they can exhibit the reduced receptor-mediated internalization or receptor-mediated clearance. Accordingly, the insulin analogs of the present invention can exhibit improved half-life in the blood compared to native insulin. The insulin analogs of the present invention include inverted insulin, derivatives of native insulin, fragments of native insulin, etc. The insulin analogs can be prepared not only by a recombinant method but also by a solid phase synthesis, and the preparation method is not limited thereto.

As used herein, the term "derivatives of native insulin" refers to a peptide which has at least one difference in the amino acid sequence compared to that of the native insulin, a peptide prepared by modification of the native insulin sequence, and a native insulin mimic which can control the in-vivo blood glucose levels like the native insulin. Such derivatives of native insulin may be those which have the function of controlling in-vivo blood glucose levels.

Specifically, the derivatives of native insulin may be prepared via modification by any one method of substitution, addition, deletion, and modification in a part of the amino acid of the native insulin, or a combination of the methods.

Specifically, the derivatives of native insulin may have a homology of 80% or higher to each of the amino acid sequences of the A-chain and the B-chain of native insulin and/or a part of the groups in an amino acid residue may be modified by chemical substitution (e.g., alpha-methylation, alpha-hydroxylation), deletion (e.g., deamination), or modification (e.g., N-methylation), etc., but are not limited thereto.

The derivatives of native insulin applied in the present invention may be prepared by a combination of various methods used for preparing derivatives.

Additionally, such modification for the preparation of the derivatives of native insulin includes a modification using L-type or D-type amino acid(s), and/or non-natural amino acid(s); and/or a modification of the native sequence or post-translational modification (e.g., methylation, acylation, ubiquitination, intermolecular covalent bond, etc.).

Additionally, those insulins in which one or more amino acids are added to the amino and/or carboxy end of the native insulin are all included.

For the substitution or insertion of the amino acid(s), not only the 20 amino acids conventionally observed in human proteins but also atypical or unnatural amino acids may be used. The commercial origin of the atypical amino acids may include Sigma-Aldrich, ChemPep, Genzyme pharmaceuticals, etc. The sequences of the peptides containing these amino acids and typical peptides may be synthesized by or purchased from commercial peptide synthesis companies, such as American Peptide Company, Bachem (USA), and Anygen (Korea), but is not particularly limited thereto.

As used herein, the term "fragments of native insulin or fragments of derivatives of native insulin" refers to a form of insulin in which at least one amino acid at the amino end or carboxy end of native insulin or a derivative of native insulin is removed. Such insulin fragment can possess the function of controlling in-vivo blood glucose levels.

Additionally, the insulin analogs of the present invention may be those which were prepared using the method(s) for preparing the derivatives and fragments of the native insulin independently or in combination.

Specifically, the insulin analogs according to the present invention may include those having a modification in the A-chain and B-chain of native insulin described above, and specifically, those in which a particular amino acid residue(s) of A-chain of native insulin is(are) modified and/or a particular amino acid residue(s) of B-chain of native insulin is(are) modified.

Specifically, the insulin analogs may be those, in which at least one modification in amino acid, which is selected from the group consisting of the 16$^{th}$ amino acid of the B-chain, the 25$^{th}$ amino acid of the B-chain, the 14$^{th}$ amino acid of the A-chain, and the 19$^{th}$ amino acid of the A-chain of native insulin, is substituted with a different amino acid, and specifically, it may be substituted with glutamic acid, serine, threonine, aspartic acid, histidine, lysine, or alanine, but is not limited thereto.

Specifically, the insulin analogs may be those, in which at least one, at least two, at least three, or four amino acids among the amino acids described above is(are) substituted with other amino acid(s).

Specifically, the modification may be a modification of the 16$^{th}$ amino acid of the B-chain of insulin (i.e., tyrosine) into glutamic acid, serine, threonine, or aspartic acid; a modification of the 25$^{th}$ amino acid of the B-chain of insulin (i.e., phenylalanine) into aspartic acid or glutamic acid; a modification of the 14$^{th}$ amino acid of the A-chain of insulin (i.e., tyrosine) into histidine, lysine, alanine, or aspartic acid; or a modification of the 19$^{th}$ amino acid of the A-chain of insulin (i.e., tyrosine) into glutamic acid, serine, or threonine.

Accordingly, the insulin analogs may include a modification of the 16$^{th}$ amino acid of the B-chain of native insulin (i.e., tyrosine) into glutamic acid, serine, threonine, or aspartic acid; and/or a modification of the 25$^{th}$ amino acid of the B-chain of native insulin (i.e., phenylalanine) into aspartic acid or glutamic acid; and/or a modification of the 14$^{th}$ amino acid of the A-chain of native insulin (i.e., tyrosine) into histidine, lysine, alanine, or aspartic acid; and/or a modification of the 19$^{th}$ amino acid of the A-chain of native insulin (i.e., tyrosine) into glutamic acid, serine, or threonine, but the modification is not limited thereto.

More specifically, the insulin analogs may be those including the A-chain of SEQ ID NO: 55 represented by General Formula 1 below and the B-chain of SEQ ID NO: 56 represented by General Formula 2 below. These insulin analogs may be in the form where the A-chain and the B-chain are interlinked by a disulfide bond, or in the form of a proinsulin, but are not limited thereto.

[General Formula 1]
(SEQ ID NO: 55)
Xaa1-Ile-Val-Glu-Xaa5-Cys-Cys-Thr-Ser-Ile-Cys- Xaa12-Leu-Xaa14-Gln-Xaa16-Glu-Asn-Xaa19-Cys- Xaa21

In General Formula 1,
Xaa1 is alanine, glycine, glutamine, histidine, glutamic acid, or asparagine,
Xaa5 is alanine, glutamic acid, glutamine, histidine, or asparagine,
Xaa12 is alanine, serine, glutamine, glutamic acid, histidine, or asparagine,
Xaa14 is tyrosine, histidine, lysine, alanine, or aspartic acid,
Xaa16 is alanine, leucine, tyrosine, histidine, glutamic acid, or asparagine,
Xaa19 is tyrosine, glutamic acid, serine, or threonine, and
Xaa21 is asparagine, glycine, histidine, or alanine.

[General Formula 2]
(SEQ ID NO: 56)
Phe-Val-Asn-Gln-His-Leu-Cys-Gly-Ser-His-Leu- Val-Glu-Ala-Leu-Xaa16-Leu-Val-Cys-Gly-Glu-Arg- Gly-Phe-Xaa25-Tyr-Xaa27-Xaa28-Lys-Thr In General Formula 2,
Xaa16 is tyrosine, glutamic acid, serine, threonine, or aspartic acid,
Xaa25 is phenylalanine, aspartic acid, or glutamic acid,
Xaa27 is threonine, or is absent, and
Xaa28 is proline, glutamic acid, or aspartic acid, or is absent.

Herein, the peptides including the A-chain of SEQ ID NO: 53 and the B-chain of SEQ ID NO: 54 may be excluded.

Additionally, those peptides which have a homology of 70% or higher, specifically 80% or higher, more specifically 90% or higher, and even more specifically 95% or higher to the sequence of the corresponding insulin analog including the A-chain of General Formula 1 above and the B-chain of General Formula 2 above, while including the characteristic modification (i.e., amino acid residues not present in native insulin) described above, specifically, the 14$^{th}$ and/or the 19$^{th}$ amino acids of the A-chain, and/or the 16$^{th}$ and/or the 25$^{th}$ amino acids of the B-chain, and have a reduced binding affinity to receptors compared to the native insulin are also included in the scope of the present invention.

As used herein, the term "homology" refers to a level of similarity with regard to the amino acid sequence of a wild type protein or a polynucleotide sequence encoding the same, and includes the sequences having a sequence with the above percentage or higher of the same sequence with the amino acid sequence or polynucleotide sequence of the present invention. This homology may be determined via comparison by the naked eye, or may be determined via a bioinformatic algorithm, which analyzes the degree of homology by arranging the two sequences. The homology between the two amino acid sequences may be indicated in percentage. Useful automated algorithms can be used at both GAP, BESTFIT, and FASTA of Wisconsin Genetics Software Package (Genetics Computer Group, Madison, Wis., USA) and TFASTA computer software module. The automated array algorithms include the sequence array algorithms of Needleman & Wunsch, Pearson & Lipman, and Smith & Waterman. The determination on algorithm and homology is automated in software including FASTP, BLAST, BLAST2, PSIBLAST, and CLUSTAL W.

In an exemplary embodiment, the insulin analog may be an insulin analog including the A-chain of SEQ ID NO: 55 represented by General Formula 1 above and the B-chain of SEQ ID NO: 54; or an insulin analog including the A-chain of SEQ ID NO: 53 and the B-chain of SEQ ID NO: 56 represented by General Formula 2 above, but is not particularly limited thereto.

More specifically, the insulin analog may be an insulin analog, wherein in General Formula 1, Xaa1 is glycine, Xaa5 is glutamine, Xaa12 is serine, Xaa14 is tyrosine, histidine, lysine, alanine, or aspartic acid, Xaa16 is leucine, Xaa19 is tyrosine, glutamic acid, serine, or threonine, and Xaa21 is asparagine; and in General Formula 2, Xaa16 is tyrosine, glutamic acid, serine, threonine, or aspartic acid, Xaa25 is phenylalanine, aspartic acid, or glutamic acid, Xaa27 is threonine, and Xaa28 is proline, but is not limited thereto.

More specifically, the insulin analog may be an insulin analog, wherein in General Formula 1, Xaa1 is glycine, Xaa5 is glutamine, Xaa12 is serine, Xaa14 is tyrosine, Xaa16 is leucine, Xaa19 is tyrosine, glutamic acid, or serine, and Xaa21 is asparagine; and in General Formula 2, Xaa16 is tyrosine, glutamic acid, serine, or aspartic acid, Xaa25 is phenylalanine, aspartic acid, or glutamic acid, Xaa27 is threonine, and Xaa28 is proline, but is not limited thereto.

More specifically, the insulin analog may be an insulin analog, wherein in General Formula 1, Xaa1 is glycine, Xaa5 is glutamine, Xaa12 is serine, Xaa14 is tyrosine or aspartic acid, Xaa16 is leucine, Xaa19 is tyrosine, glutamic acid, serine, or threonine, and Xaa21 is asparagine; and in General Formula 2, Xaa16 is tyrosine, Xaa25 is phenylalanine, aspartic acid, or glutamic acid, Xaa27 is threonine, and Xaa28 is proline, but is not limited thereto.

In an exemplary embodiment, the insulin analog according to the present invention may correspond to the following insulin analogs:

(1) in General Formula 1, Xaa1 is glycine, Xaa5 is glutamine, Xaa12 is serine, Xaa14 is histidine, Xaa16 is leucine, Xaa19 is tyrosine, and Xaa21 is asparagine; and in General Formula 2, Xaa16 is tyrosine, Xaa25 is phenylalanine, Xaa27 is threonine, and Xaa28 is proline;

(2) in General Formula 1, Xaa1 is glycine, Xaa5 is glutamine, Xaa12 is serine, Xaa14 is lysine, Xaa16 is leucine, Xaa19 is tyrosine, and Xaa21 is asparagine; and in General Formula 2, Xaa16 is tyrosine, Xaa25 is phenylalanine, Xaa27 is threonine, and Xaa28 is proline;

(3) in General Formula 1, Xaa1 is glycine, Xaa5 is glutamine, Xaa12 is serine, Xaa14 is tyrosine, Xaa16 is leucine, Xaa19 is glutamic acid, and Xaa21 is asparagine; and in General Formula 2, Xaa16 is tyrosine, Xaa25 is phenylalanine, Xaa27 is threonine, and Xaa28 is proline;

(4) in General Formula 1, Xaa1 is glycine, Xaa5 is glutamine, Xaa12 is serine, Xaa14 is tyrosine, Xaa16 is leucine, Xaa19 is serine, and Xaa21 is asparagine; and in General Formula 2, Xaa16 is tyrosine, Xaa25 is phenylalanine, Xaa27 is threonine, and Xaa28 is proline;

(5) in General Formula 1, Xaa1 is glycine, Xaa5 is glutamine, Xaa12 is serine, Xaa14 is tyrosine, Xaa16 is leucine, Xaa19 is threonine, and Xaa21 is asparagine; and in General Formula 2, Xaa16 is tyrosine, Xaa25 is phenylalanine, Xaa27 is threonine, and Xaa28 is proline;

(6) in General Formula 1, Xaa1 is glycine, Xaa5 is glutamine, Xaa12 is serine, Xaa14 is tyrosine, Xaa16 is leucine, Xaa19 is tyrosine, and Xaa21 is asparagine; and in General Formula 2, Xaa16 is glutamic acid, Xaa25 is phenylalanine, Xaa27 is threonine, and Xaa28 is proline;

(7) in General Formula 1, Xaa1 is glycine, Xaa5 is glutamine, Xaa12 is serine, Xaa14 is tyrosine, Xaa16 is leucine, Xaa19 is tyrosine, and Xaa21 is asparagine; and in General Formula 2, Xaa16 is serine, Xaa25 is phenylalanine, Xaa27 is threonine, and Xaa28 is proline;

(8) in General Formula 1, Xaa1 is glycine, Xaa5 is glutamine, Xaa12 is serine, Xaa14 is tyrosine, Xaa16 is leucine, Xaa19 is tyrosine, and Xaa21 is asparagine; and in General Formula 2, Xaa16 is threonine, Xaa25 is phenylalanine, Xaa27 is threonine, and Xaa28 is proline;

(9) in General Formula 1, Xaa1 is glycine, Xaa5 is glutamine, Xaa12 is serine, Xaa14 is alanine, Xaa16 is leucine, Xaa19 is tyrosine, and Xaa21 is asparagine; and in General Formula 2, Xaa16 is tyrosine, Xaa25 is phenylalanine, Xaa27 is threonine, and Xaa28 is proline;

(10) in General Formula 1, Xaa1 is glycine, Xaa5 is glutamine, Xaa12 is serine, Xaa14 is aspartic acid, Xaa16 is leucine, Xaa19 is tyrosine, and Xaa21 is asparagine; and in General Formula 2, Xaa16 is tyrosine, Xaa25 is phenylalanine, Xaa27 is threonine, and Xaa28 is proline;

(11) in General Formula 1, Xaa1 is glycine, Xaa5 is glutamine, Xaa12 is serine, Xaa14 is tyrosine, Xaa16 is leucine, Xaa19 is tyrosine, and Xaa21 is asparagine; and in General Formula 2, Xaa16 is aspartic acid, Xaa25 is phenylalanine, Xaa27 is threonine, and Xaa28 is proline;

(12) in General Formula 1, Xaa1 is glycine, Xaa5 is glutamine, Xaa12 is serine, Xaa14 is tyrosine, Xaa16 is leucine, Xaa19 is tyrosine, and Xaa21 is asparagine; and in General Formula 2, Xaa16 is tyrosine, Xaa25 is aspartic acid, Xaa27 is threonine, and Xaa28 is proline; and

(13) in General Formula 1, Xaa1 is glycine, Xaa5 is glutamine, Xaa12 is serine, Xaa14 is tyrosine, Xaa16 is leucine, Xaa19 is tyrosine, and Xaa21 is asparagine; and in General Formula 2, Xaa16 is tyrosine, Xaa25 is glutamic acid, Xaa27 is threonine, and Xaa28 is proline.

Additionally, in an exemplary embodiment, the insulin analog may be an insulin analog including an amino acid sequence selected from the group consisting of SEQ ID NOS: 28, 30, 32, 34, 36, 38, 40, 42, 44, 46, 48, 50, and 52, but is not limited thereto.

The insulin analog according to the present invention may be a peptide including the specific sequence described above, a peptide consisting (essentially) of the above-described specific sequence, but is not limited to.

Meanwhile, although it is described as "peptide or insulin analog consisting of a specific SEQ ID NO" in the present invention, it does not exclude any addition of nonsense sequences upstream or downstream of the amino acid sequence of the corresponding SEQ ID NO or naturally-occurring mutations, or silent mutations thereof, as long as the peptide has the same or equivalent activity as the peptide or the insulin analog consisting of the amino acid sequence of the corresponding SEQ ID NO, and it is obvious that such a sequence addition or mutation is also within the scope of the present invention.

Meanwhile, the insulin analog includes all of the peptide itself, salts thereof (e.g., a pharmaceutically acceptable salt of the peptide), or solvates thereof.

Additionally, the peptide or insulin analog may be in any pharmaceutically acceptable form.

The kind of the salt is not particularly limited. However, it is preferred that the salt be in a safe and effective form for a subject (for example, mammals), but is not particularly limited thereto.

As used herein, the term "pharmaceutically acceptable" refers to a material which can be effectively used for a desired purpose without causing excessive toxicity, irritation, allergic response, etc., within the scope of pharmacomedical decision.

As used herein, the term "pharmaceutically acceptable salt" includes a salt derived from pharmaceutically acceptable inorganic acids, organic acids, or bases. Examples of the suitable acids may include hydrochloric acid, bromic acid, sulfuric acid, nitric acid, perchloric acid, fumaric acid, maleic acid, phosphoric acid, glycolic acid, lactic acid, salicylic acid, succinic acid, toluene-p-sulfonic acid, tartaric acid, acetic acid, citric acid, methanesulfonic acid, formic acid, benzoic acid, malonic acid, naphthalene-2-sulfonic acid, benzenesulfonic acid, etc. Salts derived from suitable bases may include alkali metals such as sodium, potassium, etc., alkaline earth metals such as magnesium, etc., ammonium, etc.

Additionally, as used herein, the term "solvate" refers to a complex which is formed between the peptide according to the present invention or a salt thereof and a solvent molecule.

In another aspect, the present invention provides an isolated nucleic acid encoding the insulin analog, a recombinant expression vector including the nucleic acid, and a transformant including the recombinant expression vector.

The insulin analog is the same as explained above.

As used herein, the term "nucleic acid" refers to a deoxyribonucleotide (DNA) or ribonucleotide (RNA) present in the form of a single strand or double strand, including genomic DNA, cDNA, and RNA being transcribed therefrom, and a nucleotide as the basic constituting unit in a nucleic acid molecule not only includes natural nucleotides but also includes analogs having modifications in a sugar or base (Scheit, Nucleotide Analogs, John Wiley, New York, 1980; Uhlman and Peyman, Chemical Reviews, 90: 543-584, 1990). The nucleic acid of the present invention may be isolated or prepared using standard technology in molecular biology. For example, the nucleic acid of the present invention may be prepared by PCR amplification using appropriate primer sequences based on the gene sequence of native insulin (NM_000207.2, NCBI), and may be prepared by standard synthesis technology using an automated DNA synthesizer.

Specifically, the nucleic acid of the present invention includes the nucleotide sequences represented by SEQ ID NO: 27, 29, 31, 33, 35, 37, 39, 41, 43, 45, 47, 49, or 51. In an exemplary embodiment, the nucleic acid of the present invention not only includes the nucleotide sequences represented by SEQ ID NO: 27, 29, 31, 33, 35, 37, 39, 41, 43, 45, 47, 49, or 51, but also includes all sequences which have a sequence homology of at least 70% to the above sequences, preferably at least 80%, more preferably at least 90%, even more preferably at least 95%, and most preferably at least 98%, in which the peptide encoded by the above nucleic acid exhibits a reduced binding affinity to receptors compared to the native insulin while substantially having the function of controlling in-vivo blood glucose levels.

The recombinant vector according to the present invention may be constructed as a vector for typical cloning or for expression, and may be constructed as a vector using a eukaryotic cell or prokaryotic cell as a host cell.

As used herein, the term "vector" refers to a recombinant vector capable of expressing a target protein in an appropriate host cell, which is a nucleic acid construct including essential regulatory factors operably linked to enable the expression of a nucleic acid insert. The present invention can prepare a recombinant vector which includes a nucleic acid encoding an insulin analog, and the insulin analog of the present invention may be obtained via transformation or transfection of the recombinant vector into a host cell.

In the present invention, the nucleic acid encoding the insulin analog can be operably linked to a promoter.

As used herein, the term "operably linked" refers to a functional connection between a regulatory sequence for nucleic acid expression (e.g., a promoter, a signal sequence, a ribosome-binding site, a transcription termination sequence, etc.) and a different nucleotide sequence, and the regulatory sequence can regulate the transcription and/or translation of the different nucleotide sequence by the same.

As used herein, the term "promoter" refers to an untranslated nucleic acid sequence which may be located upstream of a coding region, includes a polymerase-binding site and has the activity of initiating transcription of a gene located downstream of a promoter into mRNA, i.e., a DNA region to which polymerase binds and initiates the transcription of a gene, and it may be located at the 5' region of mRNA transcription initiation.

For example, when the vector of the present invention is a recombinant vector and uses a prokaryotic cell as a host cell, in general, a strong promoter (e.g., tac promoter, lac promoter, lacUV5 promoter, lpp promoter, pLλ promoter, pRλ promoter, racy promoter, amp promoter, recA promoter, SP6 promoter, trp promoter, T7 promoter, etc.) capable of executing transcription, a ribosome-binding site for the initiation of translation, and transcription/translation termination sequences are generally included.

Additionally, the vector to be used in the present invention may be prepared by manipulating the plasmids (e.g., pSC101, pGV1106, pACYC177, ColE1, pKT230, pME290, pBR322, pUC8/9, pUC6, pBD9, pHC79, pIJ61, pLAFR1, pHV14, pGEX series, pET series, pPICZα series, pUC19, etc.), phages (e.g., λgt4-λB, λ-Charon, λΔz1, M13, etc.), or viruses (e.g., SV40, etc.), which are commonly used in the art.

Meanwhile, when the vector of the present invention is a recombinant vector and uses a eukaryotic cell as a host cell, promoters derived from the genomes of mammalian cells (e.g., metallothionein promoter) or promoters derived from the mammalian viruses (e.g., adenovirus late promoter, 7.5K promoter of papillomavirus, SV40 promoter, cytomegalovirus promoter, and tk promoter of HSV) may be used, and in general, the vector includes a polyadenylated sequence (e.g., bovine growth hormone terminator and a polyadenylated sequence derived from SV40) as a transcription termination sequence.

Additionally, the recombinant vector of the present invention includes an antibiotic-resistance gene commonly used in the art as a selective marker, and may include, for example, genes having resistance to ampicillin, gentamycin, carbenicillin, chloramphenicol, streptomycin, kanamycin, geneticin, neomycin, and tetracycline.

The recombinant vector of the present invention may additionally include a different sequence to facilitate the purification of target proteins being collected, i.e., a single-chain insulin analog, proinsulin, or an analog thereof. The sequence to be additionally included may be a tag sequence for protein purification, e.g., glutathione S-transferase (Pharmacia, USA), a maltose-binding protein (NEB, USA), FLAG (IBI, USA), 6-histidine, etc., but the kinds of the sequence necessary for the purification of target proteins are not limited thereto.

Fusion proteins expressed by the recombinant vector including the above tag sequence may be purified by affinity chromatography. For example, when glutathione S-transferase is fused, glutathione, which is the substrate for the enzyme, may be used, whereas when 6-histidine tag is used, a desired target protein may be easily collected by a Ni-NTA column.

As used herein, the term "transformation" refers to a process of introducing DNA into a host cell and making the DNA replicable therein as a chromosomal factor or by completion of chromosomal integration, which is a phenomenon of artificially causing a genetic change by introducing exogenous DNA into a cell.

The method of transformation used in the present invention may be any transformation method, and it may be easily performed according to the conventional method used in the art. Examples of the commonly used transformation method may include a $CaCl_2$ precipitation method, the Hanahan method with improved efficiency using dimethyl sulfoxide (DMSO) as a reducing agent in the $CaCl_2$ precipitation method, electroporation, a $CaPO_4$ precipitation method, a protoplast fusion method, a stirring method using silicon carbide fiber, an agrobacteria-mediated transformation, a transformation using PEG, dextran sulfate-, lipofectamine-, and dry/suppression-mediated transformations, etc.

The method for transforming the recombinant vector including a nucleic acid encoding an insulin analog according to the present invention may not be limited to these methods, but any method for transformation or transfection commonly used in the art may be used without limitation.

The transformant of the present invention may be obtained by introducing a recombinant vector including the target nucleic acid which encodes an insulin analog into a host cell.

An appropriate host to be used in the present invention may not be particularly limited as long as it can express the nucleic acid of the present invention. Examples of the appropriate host may include a bacteria belonging to the genus *Escherichia* such as *E. coli*, a bacteria belonging to the genus *Bacillus* such as *Bacillus subtilis*, a bacteria belonging to the genus *Pseudomonas* such as *Pseudomonas putida*, yeasts such as *Pichia pastoris, Saccharomyces cerevisiae*, and *Schizosaccharomyces pombe*, an insect cell such as *Spodoptera frugiperda* (SF9), and animal cells such as CHO, COS, and BSC. Specifically, *E. coli* may be used as a host cell, but is not limited thereto.

In another aspect to achieve the objects of the present invention, there is provided a method for preparing insulin analogs using the transformant.

Specifically, a method for preparing the insulin analog may include the following:

a) expressing an insulin analog by culturing a transformant including the nucleic acid encoding the insulin analog; and b) isolating and purifying the expressed insulin analog.

The medium used in culturing the transformants in the present invention may meet the requirements for host cell cultivation in an appropriate manner. The carbon sources to be contained in the medium for the growth of a host cell may be appropriately selected by the decision of a skilled person in the art according to the transformants prepared thereof, and appropriate cultivation conditions may be selected to control the period and amount of cultivation.

Examples of the sugar source to be used may include sugars and carbohydrates such as glucose, saccharose, lactose, fructose, maltose, starch, and cellulose; oils and fats such as soybean oil, sunflower oil, castor oil, and coconut oil; fatty acids such as palmitic acid, stearic acid, and linoleic acid; alcohols such as glycerol and ethanol; and organic acids such as acetic acid. These materials may be used alone or in combination.

Examples of the nitrogen source to be used may include peptone, yeast extract, meat gravy, malt extract, corn steep liquor, soybean flour, and urea, or inorganic compounds such as ammonium sulfate, ammonium chloride, ammonium phosphate, ammonium carbonate, and ammonium nitrate. The nitrogen source may also be used alone or in combination.

Examples of the phosphorous source to be used may include potassium dihydrogen phosphate or dipotassium hydrogen phosphate or a corresponding sodium-containing salt. Additionally, the culture media may contain a metal salt such as magnesium sulfate or iron sulfate necessary for the growth of the transformant.

Lastly, essential growth materials such as amino acids and vitamins may be used. Additionally, appropriate precursors for culture media may also be used. The above sources may be appropriately added to a culture during cultivation by a batch culture or continuous culture. The pH of the culture may be appropriately adjusted using a basic compound such as sodium hydroxide, potassium hydroxide, and ammonia, or an acid compound such as phosphoric acid or sulfuric acid. Additionally, an antifoaming agent such as fatty acid polyglycol ester may be added to prevent foam generation. Additionally, in order to maintain the aerobic state of the culture, oxygen or an oxygen-containing gas (e.g., air) may be injected into the culture.

The transformant of the present invention may be cultured at 20° C. to 45° C., and specifically, 25° C. to 40° C. Additionally, the cultivation is continued until the maximum amount of production of the desired insulin analogs is obtained, and in this regard, the cultivation may normally be continued for 10 hours to 160 hours.

As described above, the transformant of the present invention can produce insulin analogs when appropriate culture conditions are provided according to host cells, and the insulin analogs produced according to the vector constitution and characteristics of a host cell may be secreted within the cytoplasm or into the periplasmic space of the host cell or extracellularly.

The proteins expressed within or outside of the host cell may be purified by a conventional method. Examples of the purification method may include salting-out (e.g., ammonium sulfate precipitation, ammonium phosphate precipitation, etc.), solvent precipitation (e.g., protein fraction precipitation using acetone or ethanol, etc.), dialysis, gel filtration, ion exchange, or chromatography such as reversed column chromatography, ultrafiltration, etc. and these methods may be used alone or in combination.

In an exemplary embodiment, the present invention may further include the following steps for separation and purification of the insulin analog expressed in the form of inclusion bodies from the transformant:

b-1) obtaining the transformant from the culture in step a) and pulverizing the same;

b-2) recovering the expressed insulin analog from the pulverized cell lysate followed by refolding the same;

b-3) purifying the refolded insulin analog by cation exchange chromatography;

b-4) treating the purified insulin analog with trypsin and carboxypeptidase B; and b-5) sequentially purifying the treated insulin analog by cation exchange chromatography, and anion exchange chromatography or reversed-phase chromatography.

In still another aspect, the present invention provides a composition (e.g., a pharmaceutical composition) for treating diabetes containing the insulin analog as an active ingredient.

The pharmaceutical composition may be a pharmaceutical composition for treating insulin-related diseases (e.g., diabetes).

The insulin analog is the same as explained above.

As used herein, the term "insulin-related disease" refers to a disease that occurs or progresses in the absence or low level of physiological activity of insulin, for example including diabetes, but is not particularly limited thereto.

The pharmaceutical composition containing the insulin analog of the present invention may include pharmaceutically acceptable carriers.

As used herein, the term "pharmaceutically acceptable" refers to the properties of having a sufficient amount to exhibit a therapeutic effect and not causing adverse effects, and may be easily determined by a skilled person in the art based on the factors well-known in the medical field, such as the kind of disease, age, body weight, health status, sex, drug sensitivity of a patient, administration route, administration method, administration frequency, duration of treatment, a drug(s) to be mixed or administered simultaneously, etc.

For oral administration, the pharmaceutically acceptable carrier may contain a binder, a lubricant, a disintegrator, an excipient, a solubilizer, a dispersing agent, a stabilizer, a suspending agent, a coloring agent, a perfume, etc. For injectable preparations, the pharmaceutically acceptable carrier may contain a buffering agent, a preservative, an analgesic, a solubilizer, an isotonic agent, and a stabilizer. For preparations for topical administration, the pharmaceutically acceptable carrier may contain a base, an excipient, a lubricant, a preservative, etc. The pharmaceutical composition of the present invention may be formulated into various dosage forms in combination with the aforementioned pharmaceutically acceptable carriers. For example, for oral administration, the pharmaceutical composition may be formulated into tablets, troches, capsules, elixirs, suspensions, syrups, or wafers. For injectable preparations, the pharmaceutical composition may be formulated into a single-dose ampule or multidose container. The pharmaceutical composition may also be formulated into solutions, suspensions, tablets, pills, capsules, and sustained-release preparations.

Meanwhile, examples of carriers, excipients, and diluents suitable for formulation may include lactose, dextrose, sucrose, sorbitol, mannitol, xylitol, erythritol, maltitol, starch, acacia, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate, mineral oils, etc. Additionally, the pharmaceutical formulations may further contain a filler, an anti-coagulant, a lubricant, a humectant, a flavoring agent, an emulsifier, a preservative, etc.

Additionally, the insulin analogs of the present application may be included in an amount of 0.001 wt % to 10 wt % based on the total weight of the composition of the present application, but the amount is not particularly limited thereto.

In still another aspect, the present invention provides a method for treating insulin-related diseases (e.g., diabetes) including administering the insulin analog or a pharmaceutical composition containing the insulin analog to a subject in need thereof.

The insulin analog and the pharmaceutical composition are the same as explained above.

As used herein, the term "administration" refers to introduction of a particular material to a patient by an appropriate manner, and the insulin analog of the present invention may be administered by any of the common routes as long as the drug can arrive at a target tissue. For example, intraperitoneal, intravenous, intramuscular, subcutaneous, intradermal, oral, topical, intranasal, intrapulmonary, and intrarectal administration may be performed, but the administration route is not limited thereto. However, since peptides are digested upon oral administration, active ingredients of a composition for oral administration should be coated or formulated for protection against degradation in the stomach. Preferably, the present composition may be administered in an injectable form. Additionally, the pharmaceutical composition may be administered using a certain apparatus capable of transporting the active ingredients into a target cell.

Additionally, the pharmaceutical composition of the present invention may be determined by the types of the drug as an active component as well as by several related factors including the types of diseases to be treated, administration routes, age, sex, and body weight of a patient, and severity of the illness. Since the pharmaceutical composition of the present invention has excellent in-vivo duration, it can considerably reduce the administration frequency and dose of pharmaceutical drugs of the present invention.

The total effective dose of the composition of the present invention may be administered to a patient in a single dose or may be administered for a long period of time in multiple doses according to a fractionated treatment protocol. The amount of active ingredient(s) contained in the pharmaceutical composition of the present invention may vary depending on the disease severity. Specifically, the total daily dose of the insulin analog of the present invention may be about 0.0001 mg to 500 mg per 1 kg of body weight of a patient.

However, the effective dose of the insulin analog is determined considering various factors including patient's age, body weight, health conditions, sex, disease severity, diet, and excretion rate, in addition to administration route and treatment frequency of the pharmaceutical composition. In this regard, those skilled in the art may easily determine the effective dose suitable for the particular use of the pharmaceutical composition of the present invention. The pharmaceutical composition according to the present invention is not particularly limited to the formulation and administration route and mode, as long as it shows the effects of the present invention.

To achieve the present invention, another aspect of the present invention provides a use of the insulin analog in the preparation of a medicament.

In an embodiment, the medicament is for preventing or treating insulin-related diseases, but the use is not particularly limited thereto.

In an embodiment, the medicament is for preventing or treating diabetes, but the use is not particularly limited thereto.

To achieve the present invention, still another aspect of the present invention provides a use of the insulin analog in the treatment of insulin-related diseases, specifically diabetes.

The insulin analog and insulin-related diseases are the same as explained above.

Hereinafter, the present invention will be described in more detail with reference to the following examples. However, these examples are provided for illustrative purposes Example 1: Preparation of a Single-Chain Insulin Analog Expression Vector In order to prepare insulin analogs having a single modified amino acid in the A chain or the B chain, respectively, using the native insulin-expressing vector under possession as a template, forward and reverse oligonucleotides were synthesized (Table 2), and then PCR was performed to amplify each of the genes for the analogs.

The amino acid sequences modified in the A chain or the B chain and analog names are shown in Table 1 below. In Table 1, Analog 1 represents an analog in which the 14$^{th}$ amino acid of the A chain (i.e., tyrosine, Y) is substituted with histidine (H), and Analog 6 represents an analog in which the 16$^{th}$ amino acid of the B chain (i.e., tyrosine, Y) is substituted with glutamic acid (E).

TABLE 1

| Insulin Analog No. | Sequence Modification |
|---|---|
| Analog 1 | A $^{14}$Y → H |
| Analog 2 | A $^{14}$Y → K |
| Analog 3 | A $^{19}$Y → E |
| Analog 4 | A $^{19}$Y → S |
| Analog 5 | A $^{19}$Y → T |
| Analog 6 | B $^{16}$Y → E |
| Analog 7 | B $^{16}$Y → S |
| Analog 8 | B $^{16}$Y → T |
| Analog 9 | A $^{14}$Y → A |
| Analog 10 | A $^{14}$Y → D |
| Analog 11 | B $^{16}$Y → D |
| Analog 12 | B $^{25}$F → D |
| Analog 13 | B $^{25}$F → E |

Primers for insulin analog amplification are shown in Table 2 below.

TABLE 2

| Analog | Sequence | SEQ ID NO |
|---|---|---|
| Analog 1 | 5' CAGCATCTGCTCCCTCCATCAGCTGGAGAACTAC 3' | 1 |
| | 5' GTAGTTCTCCAGCTGATGGAGGGAGCAGATGCTG 3' | 2 |
| Analog 2 | 5' CAGCATCTGCTCCCTCAAGCAGCTGGAGAACTAC 3' | 3 |
| | 5' GTAGTTCTCCAGCTGCTTGAGGGAGCAGATGCTG 3' | 4 |
| Analog 3 | 5' CTACCAGCTGGAGAACGAGTGCAACTGAGGATCC 3' | 5 |
| | 5' GGATCCTCAGTTGCACTCGTTCTCCAGCTGGTAG 3' | 6 |
| Analog 4 | 5' CTACCAGCTGGAGAACTCCTGCAACTGAGGATCC 3' | 7 |
| | 5' GGATCCTCAGTTGCAGGAGTTCTCCAGCTGGTAG 3' | 8 |
| Analog 5 | 5' CTACCAGCTGGAGAACACCTGCAACTGAGGATCC 3' | 9 |
| | 5' GGATCCTCAGTTGCAGGTGTTCTCCAGCTGGTAG 3' | 10 |
| Analog 6 | 5' CTGGTGGAAGCTCTCGAGCTAGTGTGCGGGGAAC 3' | 11 |
| | 5' GTTCCCCGCACACTAGCTCGAGAGCTTCCACCAG 3' | 12 |
| Analog 7 | 5' CTGGTGGAAGCTCTCTCCCTAGTGTGCGGGGAAC 3' | 13 |
| | 5' GTTCCCCGCACACTAGGGAGAGAGCTTCCACCAG 3' | 14 |
| Analog 8 | 5' CTGGTGGAAGCTCTCACCCTAGTGTGCGGGGAAC 3' | 15 |
| | 5' GTTCCCCGCACACTAGGGTGAGAGCTTCCACCAG 3' | 16 |
| Analog 9 | 5' CAGCATCTGCTCCCTCGCCCAGCTGGAGAACTAC 3' | 17 |
| | 5' GTAGTTCTCCAGCTGGGCGAGGGAGCAGATGCTG 3' | 18 |
| Analog 10 | 5' CAGCATCTGCTCCCTCGACCAGCTGGAGAACTAC 3' | 19 |
| | 5' GTAGTTCTCCAGCTGGTCGAGGGAGCAGATGCTG 3' | 20 |
| Analog 11 | 5' CTGGTGGAAGCTCTCGACCTAGTGTGCGGGGAAC 3' | 21 |
| | 5' GTTCCCCGCACACTAGGTCGAGAGCTTCCACCAG 3' | 22 |
| Analog 12 | 5' GGGGAACGAGGCTTCGACTACACACCCAAGACC 3' | 23 |
| | 5' GGTCTTGGGTGTGTAGTCGAAGCCTCGTTCCCC 3' | 24 |
| Analog 13 | 5' GGGGAACGAGGCTTCGAGTACACACCCAAGACC 3' | 25 |
| | 5' GGTCTTGGGTGTGTACTCGAAGCCTCGTTCCCC 3' | 26 |

A PCR reaction for insulin analog amplification was performed under the conditions of 95° C. for 30 seconds, 55° C. for 30 seconds, and 68° C. for 6 minutes, for 18 repeated cycles. The insulin analog fragments obtained under the conditions were inserted into pET22b vector to be expressed as intracellular inclusion bodies, and the thus-obtained expression vectors were named as pET22b-insulin analogs 1 to 13. The expression vectors contained nucleic acids encoding amino acid sequences of insulin analogs 1 to 13 under the control of T7 promoter, and insulin analog proteins were expressed as inclusion bodies in host cells including the expression vectors.

DNA sequences and protein sequences of insulin analogs 1 to 13 are given in Table 3 below.

Each sequence modification was examined by DNA sequence analysis, and as a result, each of the insulin analogs was confirmed to have been modified in their sequences according to the intended purpose.

TABLE 3

| Analog | | Sequence | SEQ ID NO |
|---|---|---|---|
| Analog 1 | DNA | TTC GTT AAC CAA CAC TTG TGT GGC TCA CAC CTG GTG GAA GCT CTC TAC CTA GTG TGC GGG GAA CGA GGC TTC TTC TAC ACA CCC AAG ACC CGC CGG GAG GCA GAG GAC CTG CAG GTG GGG CAG GTG GAG CTG GGC GGG GGC CCT GGT GCA GGC AGC CTG CAG CCC TTG GCC CTG GAG GGG TCC CTG CAG AAG CGT GGC ATT GTG GAA CAA TGC TGT ACC AGC ATC TGC TCC CTC CAT CAG CTG GAG AAC TAC TGC AAC | 27 |
| | Protein | Phe Val Asn Gln His Leu Cys Gly Ser His Leu Val Glu Ala Leu Tyr Leu Val Cys Gly Glu Arg Gly Phe Phe Tyr Thr Pro Lys Thr Arg Arg Glu Ala Glu Asp | 28 |

TABLE 3 -continued

| Analog | | Sequence | SEQ ID NO |
|---|---|---|---|
| | | Leu Gln Val Gly Gln Val Glu Leu Gly Gly Gly Pro  Gly Ala Gly Ser Leu Gln Pro Leu Ala Leu Glu Gly Ser  Leu Gln Lys Arg Gly Ile Val Glu Gln Cys Cys Thr Ser  Ile Cys Ser Leu His Gln Leu Glu Asn Tyr Cys Asn | |
| Analog 2 | DNA | TTC GTT AAC CAA CAC TTG TGT GGC TCA  CAC CTG GTG GAA GCT CTC TAC CTA GTG  TGC GGG GAA CGA GGC TTC TTC TAC ACA  CCC AAG ACC CGC CGG GAG GCA GAG GAC  CTG CAG GTG GGG CAG GTG GAG CTG GGC  GGG GGC CCT GGT GCA GGC AGC CTG CAG  CCC TTG GCC CTG GAG GGG TCC CTG CAG  AAG CGT GGC ATT GTG GAA CAA TGC TGT  ACC AGC ATC TGC TCC CTC AAG CAG CTG  GAG AAC TAC TGC AAC | 29 |
| | Protein | Phe Val Asn Gln His Leu Cys Gly Ser His Leu Val  Glu Ala Leu Tyr Leu Val Cys Gly Glu Arg Gly Phe  Phe Tyr Thr Pro Lys Thr Arg Arg Glu Ala Glu Asp  Leu Gln Val Gly Gln Val Glu Leu Gly Gly Gly Pro  Gly Ala Gly Ser Leu Gln Pro Leu Ala Leu Glu Gly Ser  Leu Gln Lys Arg Gly Ile Val Glu Gln Cys Cys Thr Ser  Ile Cys Ser Leu Lys Gln Leu Glu Asn Tyr Cys Asn | 30 |
| Analog 3 | DNA | TTC GTT AAC CAA CAC TTG TGT GGC TCA  CAC CTG GTG GAA GCT CTC TAC CTA GTG  TGC GGG GAA CGA GGC TTC TTC TAC ACA  CCC AAG ACC CGC CGG GAG GCA GAG GAC  CTG CAG GTG GGG CAG GTG GAG CTG GGC  GGG GGC CCT GGT GCA GGC AGC CTG CAG  CCC TTG GCC CTG GAG GGG TCC CTG CAG  AAG CGT GGC ATT GTG GAA CAA TGC TGT  ACC AGC ATC TGC TCC CTC TAC CAG CTG  GAG AAC GAG TGC AAC | 31 |
| | Protein | Phe Val Asn Gln His Leu Cys Gly Ser His Leu Val  Glu Ala Leu Tyr Leu Val Cys Gly Glu Arg Gly Phe  Phe Tyr Thr Pro Lys Thr Arg Arg Glu Ala Glu Asp  Leu Gln Val Gly Gln Val Glu Leu Gly Gly Gly Pro  Gly Ala Gly Ser Leu Gln Pro Leu Ala Leu Glu Gly Ser  Leu Gln Lys Arg Gly Ile Val Glu Gln Cys Cys Thr Ser  Ile Cys Ser Leu Tyr Gln Leu Glu Asn Glu Cys Asn  TTC GTT AAC CAA CAC TTG TGT GGC TCA | 32 |
| Analog 4 | DNA | CAC CTG GTG GAA GCT CTC TAC CTA GTG  TGC GGG GAA CGA GGC TTC TTC TAC ACA  CCC AAG ACC CGC CGG GAG GCA GAG GAC  CTG CAG GTG GGG CAG GTG GAG CTG GGC  GGG GGC CCT GGT GCA GGC AGC CTG CAG  CCC TTG GCC CTG GAG GGG TCC CTG CAG  AAG CGT GGC ATT GTG GAA CAA TGC TGT  ACC AGC ATC TGC TCC CTC TAC CAG CTG  GAG AAC TCC TGC AAC | 33 |
| | Protein | Phe Val Asn Gln His Leu Cys Gly Ser His Leu Val  Glu Ala Leu Tyr Leu Val Cys Gly Glu Arg Gly Phe  Phe Tyr Thr Pro Lys Thr Arg Arg Glu Ala Glu Asp  Leu Gln Val Gly Gln Val Glu Leu Gly Gly Gly Pro  Gly Ala Gly Ser Leu Gln Pro Leu Ala Leu Glu Gly Ser  Leu Gln Lys Arg Gly Ile Val Glu Gln Cys Cys Thr Ser  Ile Cys Ser Leu Tyr Gln Leu Glu Asn Ser Cys Asn | 34 |
| Analog 5 | DNA | TTC GTT AAC CAA CAC TTG TGT GGC TCA  CAC CTG GTG GAA GCT CTC TAC CTA GTG  TGC GGG GAA CGA GGC TTC TTC TAC ACA  CCC AAG ACC CGC CGG GAG GCA GAG GAC  CTG CAG GTG GGG CAG GTG GAG CTG GGC  GGG GGC CCT GGT GCA GGC AGC CTG CAG  CCC TTG GCC CTG GAG GGG TCC CTG CAG  AAG CGT GGC ATT GTG GAA CAA TGC TGT  ACC AGC ATC TGC TCC CTC TAC CAG CTG  GAG AAC ACC TGC AAC | 35 |
| | Protein | Phe Val Asn Gln His Leu Cys Gly Ser His Leu Val  Glu Ala Leu Tyr Leu Val Cys Gly Glu Arg Gly Phe  Phe Tyr Thr Pro Lys Thr Arg Arg Glu Ala Glu Asp  Leu Gln Val Gly Gln Val Glu Leu Gly Gly Gly Pro  Gly Ala Gly Ser Leu Gln Pro Leu Ala Leu Glu Gly Ser  Leu Gln Lys Arg Gly Ile Val Glu Gln Cys Cys Thr Ser  Ile Cys Ser Leu Tyr Gln Leu Glu Asn Thr Cys Asn | 36 |

TABLE 3 -continued

| Analog | Sequence | | SEQ ID NO |
|---|---|---|---|
| Analog 6 | DNA | TTC GTT AAC CAA CAC TTG TGT GGC TCA<br>CAC CTG GTG GAA GCT CTC GAG CTA GTG<br>TGC GGG GAA CGA GGC TTC TTC TAC ACA<br>CCC AAG ACC CGC CGG GAG GCA GAG GAC<br>CTG CAG GTG GGG CAG GTG GAG CTG GGC<br>GGG GGC CCT GGT GCA GGC AGC CTG CAG<br>CCC TTG GCC CTG GAG GGG TCC CTG CAG<br>AAG CGT GGC ATT GTG GAA CAA TGC TGT<br>ACC AGC ATC TGC TCC CTC TAC CAG CTG<br>GAG AAC TAC TGC AAC | 37 |
| | Protein | Phe Val Asn Gln His Leu Cys Gly Ser His Leu Val<br>Glu Ala Leu Glu Leu Val Cys Gly Glu Arg Gly Phe<br>Phe Tyr Thr Pro Lys Thr Arg Arg Glu Ala Glu Asp<br>Leu Gln Val Gly Gln Val Glu Leu Gly Gly Gly Pro<br>Gly Ala Gly Ser Leu Gln Pro Leu Ala Leu Glu Gly Ser<br>Leu Gln Lys Arg Gly Ile Val Glu Gln Cys Cys Thr Ser<br>Ile Cys Ser Leu Tyr Gln Leu Glu Asn Tyr Cys Asn | 38 |
| Analog 7 | DNA | TTC GTT AAC CAA CAC TTG TGT GGC TCA<br>CAC CTG GTG GAA GCT CTC TCC CTA GTG<br>TGC GGG GAA CGA GGC TTC TTC TAC ACA<br>CCC AAG ACC CGC CGG GAG GCA GAG GAC<br>CTG CAG GTG GGG CAG GTG GAG CTG GGC<br>GGG GGC CCT GGT GCA GGC AGC CTG CAG<br>CCC TTG GCC CTG GAG GGG TCC CTG CAG<br>AAG CGT GGC ATT GTG GAA CAA TGC TGT<br>ACC AGC ATC TGC TCC CTC TAC CAG CTG<br>GAG AAC TAC TGC AAC | 39 |
| | Protein | Phe Val Asn Gln His Leu Cys Gly Ser His Leu Val<br>Glu Ala Leu Ser Leu Val Cys Gly Glu Arg Gly Phe<br>Phe Tyr Thr Pro Lys Thr Arg Arg Glu Ala Glu Asp<br>Leu Gln Val Gly Gln Val Glu Leu Gly Gly Gly Pro<br>Gly Ala Gly Ser Leu Gln Pro Leu Ala Leu Glu Gly Ser<br>Leu Gln Lys Arg Gly Ile Val Glu Gln Cys Cys Thr Ser<br>Ile Cys Ser Leu Tyr Gln Leu Glu Asn Tyr Cys Asn | 40 |
| Analog 8 | DNA | TTC GTT AAC CAA CAC TTG TGT GGC TCA<br>CAC CTG GTG GAA GCT CTC ACC CTA GTG<br>TGC GGG GAA CGA GGC TTC TTC TAC ACA<br>CCC AAG ACC CGC CGG GAG GCA GAG GAC<br>CTG CAG GTG GGG CAG GTG GAG CTG GGC<br>GGG GGC CCT GGT GCA GGC AGC CTG CAG<br>CCC TTG GCC CTG GAG GGG TCC CTG CAG<br>AAG CGT GGC ATT GTG GAA CAA TGC TGT<br>ACC AGC ATC TGC TCC CTC TAC CAG CTG<br>GAG AAC TAC TGC AAC | 41 |
| | Protein | Phe Val Asn Gln His Leu Cys Gly Ser His Leu Val<br>Glu Ala Leu Thr Leu Val Cys Gly Glu Arg Gly Phe<br>Phe Tyr Thr Pro Lys Thr Arg Arg Glu Ala Glu Asp<br>Leu Gln Val Gly Gln Val Glu Leu Gly Gly Gly Pro<br>Gly Ala Gly Ser Leu Gln Pro Leu Ala Leu Glu Gly Ser<br>Leu Gln Lys Arg Gly Ile Val Glu Gln Cys Cys Thr Ser<br>Ile Cys Ser Leu Tyr Gln Leu Glu Asn Tyr Cys Asn | 42 |
| Analog 9 | DNA | TTC GTT AAC CAA CAC TTG TGT GGC TCA<br>CAC CTG GTG GAA GCT CTC TAC CTA GTG<br>TGC GGG GAA CGA GGC TTC TTC TAC ACA<br>CCC AAG ACC CGC CGG GAG GCA GAG GAC<br>CTG CAG GTG GGG CAG GTG GAG CTG GGC<br>GGG GGC CCT GGT GCA GGC AGC CTG CAG<br>CCC TTG GCC CTG GAG GGG TCC CTG CAG<br>AAG CGT GGC ATT GTG GAA CAA TGC TGT<br>ACC AGC ATC TGC TCC CTC GCC CAG CTG<br>GAG AAC TAC TGC AAC | 43 |
| | Protein | Phe Val Asn Gln His Leu Cys Gly Ser His Leu Val<br>Glu Ala Leu Tyr Leu Val Cys Gly Glu Arg Gly Phe<br>Phe Tyr Thr Pro Lys Thr Arg Arg Glu Ala Glu Asp<br>Leu Gln Val Gly Gln Val Glu Leu Gly Gly Gly Pro<br>Gly Ala Gly Ser Leu Gln Pro Leu Ala Leu Glu Gly Ser<br>Leu Gln Lys Arg Gly Ile Val Glu Gln Cys Cys Thr Ser<br>Ile Cys Ser Leu Ala Gln Leu Glu Asn Tyr Cys Asn | 44 |
| Analog 10 | DNA | TTC GTT AAC CAA CAC TTG TGT GGC TCA<br>CAC CTG GTG GAA GCT CTC TAC CTA GTG<br>TGC GGG GAA CGA GGC TTC TTC TAC ACA | 45 |

TABLE 3 -continued

| Analog | | Sequence | SEQ ID NO |
|---|---|---|---|
| | | CCC AAG ACC CGC CGG GAG GCA GAG GAC<br>CTG CAG GTG GGG CAG GTG GAG CTG GGC<br>GGG GGC CCT GGT GCA GGC AGC CTG CAG<br>CCC TTG GCC CTG GAG GGG TCC CTG CAG<br>AAG CGT GGC ATT GTG GAA CAA TGC TGT<br>ACC AGC ATC TGC TCC CTC GAC CAG CTG<br>GAG AAC TAC TGC AAC | |
| | Protein | Phe Val Asn Gln His Leu Cys Gly Ser His Leu Val<br>Glu Ala Leu Tyr Leu Val Cys Gly Glu Arg Gly Phe<br>Phe Tyr Thr Pro Lys Thr Arg Arg Glu Ala Glu Asp<br>Leu Gln Val Gly Gln Val Glu Leu Gly Gly Gly Pro<br>Gly Ala Gly Ser Leu Gln Pro Leu Ala Leu Glu Gly Ser<br>Leu Gln Lys Arg Gly Ile Val Glu Gln Cys Cys Thr Ser<br>Be Cys Ser Leu Asp Gln Leu Glu Asn Tyr Cys Asn | 46 |
| Analog 11 | DNA | TTC GTT AAC CAA CAC TTG TGT GGC TCA<br>CAC CTG GTG GAA GCT CTC GAC CTA GTG<br>TGC GGG GAA CGA GGC TTC TTC TAC ACA<br>CCC AAG ACC CGC CGG GAG GCA GAG GAC<br>CTG CAG GTG GGG CAG GTG GAG CTG GGC<br>GGG GGC CCT GGT GCA GGC AGC CTG CAG<br>CCC TTG GCC CTG GAG GGG TCC CTG CAG<br>AAG CGT GGC ATT GTG GAA CAA TGC TGT<br>ACC AGC ATC TGC TCC CTC TAC CAG CTG<br>GAG AAC TAC TGC AAC | 47 |
| | Protein | Phe Val Asn Gln His Leu Cys Gly Ser His Leu Val<br>Glu Ala Leu Asp Leu Val Cys Gly Glu Arg Gly Phe<br>Phe Tyr Thr Pro Lys Thr Arg Arg Glu Ala Glu Asp<br>Leu Gln Val Gly Gln Val Glu Leu Gly Gly Gly Pro<br>Gly Ala Gly Ser Leu Gln Pro Leu Ala Leu Glu Gly Ser<br>Leu Gln Lys Arg Gly Ile Val Glu Gln Cys Cys Thr Ser<br>Ile Cys Ser Leu Tyr Gln Leu Glu Asn Tyr Cys Asn | 48 |
| Analog 12 | DNA | TTC GTT AAC CAA CAC TTG TGT GGC TCA<br>CAC CTG GTG GAA GCT CTC TAC CTA GTG<br>TGC GGG GAA CGA GGC TTC GAC TAC ACA<br>CCC AAG ACC CGC CGG GAG GCA GAG GAC<br>CTG CAG GTG GGG CAG GTG GAG CTG GGC<br>GGG GGC CCT GGT GCA GGC AGC CTG CAG<br>CCC TTG GCC CTG GAG GGG TCC CTG CAG<br>AAG CGT GGC ATT GTG GAA CAA TGC TGT<br>ACC AGC ATC TGC TCC CTC TAC CAG CTG<br>GAG AAC TAC TGC AAC | 49 |
| | Protein | Phe Val Asn Gln His Leu Cys Gly Ser His Leu Val<br>Glu Ala Leu Tyr Leu Val Cys Gly Glu Arg Gly Phe<br>Asp Tyr Thr Pro Lys Thr Arg Arg Glu Ala Glu Asp<br>Leu Gln Val Gly Gln Val Glu Leu Gly Gly Gly Pro<br>Gly Ala Gly Ser Leu Gln Pro Leu Ala Leu Glu Gly Ser<br>Leu Gln Lys Arg Gly Ile Val Glu Gln Cys Cys Thr Ser<br>Ile Cys Ser Leu Tyr Gln Leu Glu Asn Tyr Cys Asn | 50 |
| Analog 13 | DNA | TTC GTT AAC CAA CAC TTG TGT GGC TCA<br>CAC CTG GTG GAA GCT CTC TAC CTA GTG<br>TGC GGG GAA CGA GGC TTC GAG TAC ACA<br>CCC AAG ACC CGC CGG GAG GCA GAG GAC<br>CTG CAG GTG GGG CAG GTG GAG CTG GGC<br>GGG GGC CCT GGT GCA GGC AGC CTG CAG<br>CCC TTG GCC CTG GAG GGG TCC CTG CAG<br>AAG CGT GGC ATT GTG GAA CAA TGC TGT<br>ACC AGC ATC TGC TCC CTC TAC CAG CTG<br>GAG AAC TAC TGC AAC | 51 |
| | Protein | Phe Val Asn Gln His Leu Cys Gly Ser His Leu Val<br>Glu Ala Leu Tyr Leu Val Cys Gly Glu Arg Gly Phe<br>Glu Tyr Thr Pro Lys Thr Arg Arg Glu Ala Glu Asp<br>Leu Gln Val Gly Gln Val Glu Leu Gly Gly Gly Pro<br>Gly Ala Gly Ser Leu Gln Pro Leu Ala Leu Glu Gly Ser<br>Leu Gln Lys Arg Gly Ile Val Glu Gln Cys Cys Thr Ser<br>Ile Cys Ser Leu Tyr Gln Leu Glu Asn Tyr Cys Asn | 52 |

Example 2: Expression of Recombinant Insulin Analog Fusion Peptides

Expressions of recombinant insulin analogs were performed under the control of T7 promoter. *E. coli* BL21-DE3 (*E. coli* B F-dcm ompT hsdS(rB-mB-) gal λDE3; Novagen) was transformed with each of the recombinant insulin analog-expressing vectors. Transformation was performed in accordance with the recommended protocol (Novagen). Single colonies transformed with each recombinant expression vector were collected, inoculated in 2× Luria Broth (LB) containing ampicillin (50 μg/mL), and cultured at 37° C. for 15 hours. The recombinant strain culture broth and 2× LB medium containing 30% glycerol were mixed in a ratio of 1:1 (v/v), 1 mL each of the mixture was dispensed to a cryotube and stored at −140° C., which was used as a cell stock for producing the recombinant fusion protein.

To express the recombinant insulin analogs, one vial of each cell stock was thawed and inoculated into 500 mL of 2× Luria broth, and cultured with shaking at 37° C. for 14 hours to 16 hours. The cultivation was terminated when OD600 reached 5.0 or higher and the culture broth was used as a seed culture broth. The seed culture broth was inoculated to 17 L of fermentation medium using a 50 L fermentor (MSJ-U2, B.E.MARUBISHI, Japan), and initial bath fermentation was started. The culture conditions were maintained at a temperature of 37° C., an air flow rate of 20 L/min (1 vvm), an agitation speed of 500 rpm, and at pH 6.70 using a 30% ammonia solution. Fermentation was performed in fed-batch mode by adding a feeding solution, when nutrients were depleted in the culture broth. Growth of the strain was monitored by OD value. IPTG was introduced to a final concentration of 500 μM, when OD value reached 100 or higher. After introduction, the cultivation was progressed further for about 23 hours to 25 hours. Upon termination of the cultivation, the recombinant strains were harvested by centrifugation and stored at −80° C. until use.

Example 3: Recovery and Refolding of Recombinant Insulin Analogs

In order to change the recombinant insulin analogs expressed in Example 2 into soluble forms, cells were disrupted followed by refolding. The cell pellet (100 g; wet weight) was resuspended in 1 L lysis buffer (50 mM Tris-HCl (pH 9.0), 1 mM EDTA (pH 8.0), 0.2 M NaCl, and 0.5% Triton X-100). The cells were disrupted using a microfluidizer (Microfluidic Corp. Model M-110EH-30) at an operating pressure of 15,000 psi. The thus-disrupted cell lysate was centrifuged at 7,000 rpm at a temperature of 4° C. to 8° C. for 20 minutes. The supernatant was discarded and the pellet was resuspended in 3 L washing buffer (0.5% Triton X-100 and 50 mM Tris-HCl (pH 8.0), 0.2 M NaCl, and 1 mM EDTA). After centrifugation at 7,000 rpm at a temperature of 4° C. to 8° C. for 20 minutes, the cell pellet was resuspended in distilled water, followed by centrifugation in the same manner. The thus-obtained pellet was resuspended in buffer (1 M L-Glycine, 3.78 g L-Cysteine-HCl, pH 10.6) and stirred at room temperature for 1 hour. To recover the recombinant insulin analog thus resuspended, 8 M urea was added thereto and stirred for 3 hours to 5 hours. For refolding of the solubilized recombinant proinsulin analogs, centrifugation was carried out at 7,000 rpm at a temperature of 4° C. to 8° C. for 30 minutes, the supernatant was collected, and treated with 15 mM L-Cysteine-HCl, i.e., a reducing agent, for one hour. A predetermined volume of distilled water was added thereto using a peristaltic pump and stirred at a temperature of 4° C. to 8° C. for at least 12 hours.

Example 4: Cation Exchange Chromatography Purification

The sample, upon completion of refolding, was loaded onto an equilibrated SP FF (GE healthcare) column equilibrated with 20 mM sodium citrate (pH 2.0) buffer containing 45% ethanol, and then the insulin analog proteins were eluted in 10 column volumes with a linear gradient from 0% to 100% using a 20 mM sodium citrate (pH 2.0) buffer containing 0.5 M potassium chloride and 45% ethanol.

Example 5: Treatment with Trypsin and Carboxypeptidase B

Salts were removed from the eluted samples using an ultrafiltration membrane, followed by replacement of a buffer solution (10 mM Tris-HCl, pH 8.0). The thus-obtained sample protein was treated with trypsin corresponding to a molar ratio of about 30,000 relative to the protein amount of the sample and carboxypeptidase B corresponding to a molar ratio of about 3,000 molar ratio relative to the protein amount of the sample and stirred at a temperature of 4° C. to 8° C. for at least 16 hours.

Example 6: Cation Exchange Chromatography Purification

The sample, upon completion of the reaction, was reloaded onto an equilibrated SP HP (GE healthcare) column equilibrated with 20 mM sodium citrate (pH 2.0) buffer containing 45% ethanol, and the insulin analog proteins were eluted in 10 column volumes with a linear gradient from 0% to 100% using a 20 mM sodium citrate (pH 2.0) buffer containing 0.5 M potassium chloride and 45% ethanol.

Example 7: Reversed Phase Chromatography Purification

For the pure separation of the pure insulin analog obtained in Example 6, it was loaded onto the reversed phase chromatography Source30RPC (GE healthcare, USA), which was equilibrated with sodium phosphate and isopropanol, and the insulin analog proteins were eluted with a linear gradient using a buffer containing sodium phosphate and isopropanol.

The thus-purified insulin analogs were analyzed by protein electrophoresis (SDS-PAGE, FIG. 1) and HPLC, and among them, the purities of the representative insulin analog nos. 9, 10, 11, and 12 were analyzed and the results are shown in FIGS. 2a-2d.

Example 8: Comparison of Binding Affinity of Insulin Analogs for Insulin Receptors For the measurement of binding affinity of insulin analogs to insulin receptors, the analysis was performed by Scintillation proximity assay (SPA). The cell membrane of a CHO cell line, in which insulin receptors were expressed, and PVT SPA beads were added together into a 96-well picoplate. In order to confirm the binding affinity to the insulin receptors, human insulin and each of the insulin analogs diluted in more than 10 different concentrations, and radio-isotope $I^{125}$-tagged insulin, as a competitor, were added together and allowed to react competitively at room temperature for 4 hours. Four hours thereafter, the binding affinity to insulin receptors was measured using a beta counter. The binding affinity of each material was calculated in $IC_{50}$ using the GraphPad Prism 6 software, and digitized as the relative binding affinity against the human insulin to the insulin receptors.

As a result, compared to the human insulin, the binding affinity to the insulin receptors was shown to be 90% for insulin analog (no. 1); 95% for insulin analog (no. 2); 1.0% for insulin analog (no. 3); <0.1% for insulin analog (no. 4); 20% for insulin analog (no. 6); 8.5% for insulin analog (no. 7); 79% for insulin analog (no. 9), 79% for insulin analog (no. 10); 24% for insulin analog (no. 11); <0.1% for insulin analog (no. 12); and <0.1% for insulin analog (no. 13) (Table 4). Accordingly, the insulin analogs of the present invention were observed to have reduced binding affinity to insulin receptors compared to the native insulin.

TABLE 4

| Material Name | | Binding Affinity to Insulin Receptors (vs. Human Insulin) |
|---|---|---|
| Insulin analog | insulin analog (No. 1) | 90% |
| | insulin analog (No. 2) | 95% |
| | insulin analog (No. 3) | 1.0% |
| | insulin analog (No. 4) | <0.1% |
| | insulin analog (No. 6) | 20% |
| | insulin analog (No. 7) | 8.5% |
| | insulin analog (No. 9) | 79% |
| | insulin analog (No. 10) | 79% |
| | insulin analog (No. 11) | 24% |
| | insulin analog (No. 12) | <0.1% |
| | insulin analog (No. 13) | <0.1% |

Example 9: Comparison of In-Vitro Efficacy of Insulin Analog 10

In order to evaluate in-vitro efficacy of the insulin analog 10, mouse-derived 3T3-L1 cell line differentiated into adipocytes were used to test glucose uptake ability or lipid synthesis. 3T3-L1 cells were subcultured in 10% newborn calf serum (NBCS)-containing Dulbeco's Modified Eagle's Medium (DMEM, Gibco, Cat. No, 12430) 2 or 3 times a week, and maintained. The 3T3-L1 cells were suspended in a differentiation medium (10% FBS-containing DMEM), and then inoculated at a concentration of $5 \times 10^4$ cells per well in a 48-well dish, and cultured for 48 hours. For differentiation of the cells into adipocytes, 1 μg/mL human insulin (Sigma, Cat. No. 19278), 0.5 μM 3-isobutyl-1-methylxanthine (IBMX, Sigma, Cat. No. 15879), and 1 μM dexamethasone (Sigma, Cat. No. D4902) were mixed with the differentiation medium, and 250 μL of the mixture was added to each well, after removing the existing medium. After 48 hours, the medium was replaced with the differentiation medium supplemented with only 1 μg/mL of human insulin. Thereafter, the induction of differentiation into adipocytes was examined for 12 days while exchanging the medium with the differentiation medium supplemented with 1 μg/mL of human insulin every 48 hours. To test glucose uptake ability, the differentiated cells were washed with serum-free DMEM medium once, and then 250 μL each of serum-free DMEM medium was added to induce serum depletion for 4 hours. Serum-free DMEM medium was used to perform 10-fold serial dilutions for human insulin and insulin analog 10 from 10 μM to 0.001 nM. 250 μL each of the thus-prepared samples was added to cells, and cultured in a 5% $CO_2$ incubator at 37° C. for 24 hours. In order to measure the remaining amount of glucose in the medium after incubation, 200 μL each of the medium was taken and diluted 5-fold with D-PBS, followed by GOPOD assay (GOPOD Assay Kit, Megazyme, Cat. No. K-GLUC). Based on the absorbance of glucose standard solution, the concentration of glucose remaining in the medium was converted, and $EC_{50}$ values for glucose uptake ability of human insulin and insulin analog 10 were calculated, respectively.

A total of 3 tests were repeated, and as a result, the $EC_{50}$ values of human insulin and insulin analog 10 were calculated as 14.4±1.0 nM and 7.8±0.7 nM, respectively. That is, it was confirmed that insulin analog 10 had a glucose uptake ability of 185.5±25.7% in comparison with human insulin (FIG. 3).

Example 10: Comparison of Cell Stability of Insulin Analog 10

In order to confirm the cell stability of insulin analog 10, a test was performed using a human-derived HepG2 cell line. First, HepG2 cells were subcultured in DMEM medium containing 10% FBS 2 to 3 times a week. 300 μL each of poly-L-lysine (Trevigen, Cat. No. 3438-100-01) was added into a 24-well plate and coated at 37° C. for 2 hours. After washing twice with cold D-PBS, HepG2 cells were suspended in a culture medium (DMEM containing 10% FBS) and inoculated on a 24-well plate at a concentration of $1 \times 10^5$ cells per well and cultured for 24 hours. After washing the cells with a test medium (DMEM containing 2% FBS), 500 μL of a test medium containing 500 nM of human insulin and insulin analog 10 was added to each well. After incubating the cells in a 5% $CO_2$ incubator at 37° C. for 0, 2, 6, 9, 24, and 48 hours, the medium was recovered and stored frozen upon completion of incubation. For determining the amount of insulin remaining in the medium, a 100-fold dilution with PBS-T was performed and analyzed using the human insulin ELISA kit (Alpco, Cat. No. 80-INSHU-E10.1).

A total of 3 tests were repeated, and as a result, the amount of insulin remaining in the culture medium was calculated as 20.9±11.4% and 72.7±5.7% for human insulin and insulin analog 10, respectively, after incubating for 48 hours compared to 0 hours. That is, it was confirmed that insulin analog 10 had higher cell stability compared to human insulin (FIG. 4).

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

The invention claimed is:

1. An insulin analog comprising an A-chain of SEQ ID NO: 55 of the following Formula 1 and a B-chain of SEQ ID NO: 56 of the following Formula 2, wherein the insulin analog shows binding affinity to insulin receptors of about 99% or less and about 75% or greater, with respect to the binding affinity of native insulin to insulin receptors, as evaluated by Scintillation proximity assay (SPA), the binding affinity of native insulin to insulin receptors being 100%:

```
Formula 1                                   (SEQ ID NO: 55)
Xaa1-Ile-Val-Glu-Xaa5-Cys-Cys-Thr-Ser-Ile-Cys-
Xaa12-Leu-Xaa14-Gln-Xaa16-Glu-Asn-Xaa19-Cys-Xaa21

Formula 2                                   (SEQ ID NO: 56)
Phe-Val-Asn-Gln-His-Leu-Cys-Gly-Ser-His-Leu-Val-Glu
-Ala-Leu-Xaa16-Leu-Val-Cys-Gly-Glu-Arg-Gly-Phe-
Xaa25-Tyr-Xaa27-Xaa28-Lys-Thr,
``` wherein
(1) in Formula 1, Xaa1 is glycine, Xaa5 is glutamine, Xaa12 is serine, Xaa14 is histidine, Xaa16 is leucine, Xaa19 is tyrosine, and Xaa21 is asparagine; and in Formula 2, Xaa16 is tyrosine, Xaa25 is phenylalanine, Xaa27 is threonine, and Xaa28 is proline;
(2) in Formula 1, Xaa1 is glycine, Xaa5 is glutamine, Xaa12 is serine, Xaa14 is lysine, Xaa16 is leucine, Xaa19 is tyrosine, and Xaa21 is asparagine; and in Formula 2, Xaa16 is tyrosine, Xaa25 is phenylalanine, Xaa27 is threonine, and Xaa28 is proline;
(3) in Formula 1, Xaa1 is glycine, Xaa5 is glutamine, Xaa12 is serine, Xaa14 is alanine, Xaa16 is leucine, Xaa19 is tyrosine, and Xaa21 is asparagine; and in Formula 2, Xaa16 is tyrosine, Xaa25 is phenylalanine, Xaa27 is threonine, and Xaa28 is proline; or
(4) in Formula 1, Xaa1 is glycine, Xaa5 is glutamine, Xaa12 is serine, Xaa14 is aspartic acid, Xaa16 is leucine, Xaa19 is tyrosine, and Xaa21 is asparagine; and in Formula 2, Xaa16 is tyrosine, Xaa25 is phenylalanine, Xaa27 is threonine, and Xaa28 is proline.

2. The insulin analog of claim 1, comprising an amino acid sequence selected from the group consisting of SEQ ID NOS: 28, 30, 44, and 46.

3. The insulin analog of claim 1, wherein in Formula 1, Xaa1 is glycine, Xaa5 is glutamine, Xaa12 is serine, Xaa14 is aspartic acid, Xaa16 is leucine, Xaa19 is tyrosine, and Xaa21 is asparagine; and in Formula 2, Xaa16 is tyrosine, Xaa25 is phenylalanine, Xaa27 is threonine, and Xaa28 is proline.

4. An isolated nucleic acid encoding the insulin analog of claim 1.

5. A recombinant expression vector comprising the nucleic acid of claim 4.

6. A transformant comprising the recombinant expression vector of claim 5.

7. The transformant of claim 6, wherein the transformant is *E. coli*.

8. A method of preparing the insulin analog of claim 1 comprising:
   a) expressing the insulin analog of claim 1 by culturing a transformant comprising a nucleic acid encoding the insulin analog; and
   b) isolating and purifying the expressed insulin analog.

9. The method of preparing the insulin analog of claim 8, wherein the b) the isolating and purifying comprise:
   b-1) obtaining the transformant from the culture in step a) and pulverizing the same;
   b-2) recovering the expressed insulin analog from the pulverized cell lysate followed by refolding the same;
   b-3) purifying the refolded insulin analog by cation exchange chromatography;
   b-4) treating the purified insulin analog with trypsin and carboxypeptidase B; and
   b-5) sequentially purifying the treated insulin analog by cation exchange chromatography, and anion exchange chromatography or reversed-phase chromatography.

10. A composition comprising the insulin analog of claim 1 as an active ingredient.

11. A method for treating a subject with diabetes, including administering the insulin analog of claim 1 or a composition containing the same to the subject.

* * * * *